(12) United States Patent
Lenker et al.

(10) Patent No.: US 11,786,265 B1
(45) Date of Patent: Oct. 17, 2023

(54) STEERABLE MICROCATHETER AND METHOD OF USE

(71) Applicant: Indian Wells Medical, Inc., Lake Forest, CA (US)

(72) Inventors: Jay Alan Lenker, Lake Forest, CA (US); James Alexander Carroll, Long Beach, CA (US); Eugene Michael Breznock, Winters, CA (US); Donald J. Kolehmainen, Laguna Niguel, CA (US)

(73) Assignee: Indian Wells Medical, Inc., Lake Forest, CA (US)

( * ) Notice: Subject to any disclaimer, the term of this patent is extended or adjusted under 35 U.S.C. 154(b) by 0 days.

(21) Appl. No.: 17/877,731

(22) Filed: Jul. 29, 2022

Related U.S. Application Data

(60) Provisional application No. 63/227,905, filed on Jul. 30, 2021.

(51) Int. Cl.
*A61B 17/34* (2006.01)
*A61B 17/32* (2006.01)

(52) U.S. Cl.
CPC .......... *A61B 17/32* (2013.01); *A61B 17/3417* (2013.01); *A61B 17/3496* (2013.01)

(58) Field of Classification Search
CPC .......... A61M 25/0138; A61M 25/0141; A61M 25/0147; A61M 25/0113; A61M 2025/0161; A61B 17/32; A61B 17/3417; A61B 17/3496
See application file for complete search history.

(56) References Cited

U.S. PATENT DOCUMENTS

| 5,228,441 A | * | 7/1993 | Lundquist | A61B 18/1492 |
| | | | | 607/116 |
| 2017/0259041 A1 | * | 9/2017 | Lenker | A61M 25/09041 |

* cited by examiner

*Primary Examiner* — Rebecca E Eisenberg
*Assistant Examiner* — Justin L Zamory
(74) *Attorney, Agent, or Firm* — Crockett & Crockett, PC; K. David Crockett, Esq.

(57) ABSTRACT

A transvascularly placed steerable microcatheter, further including internal steerability and the ability to articulate in a direction at right angles to its longitudinal axis at or near its distal end. The steerable microcatheter is generally fabricated from stainless steel, nitinol, or other metal and includes an outer tube, an inner tube, hub structures, and a distal articulating region. The steerable microcatheter can be advanced through a body lumen in its straight configuration and then be selectively articulated or curved to permit negotiation of tortuous curvature. The microcatheter is especially suited to robotic or powered control applications with user intervention or using artificial intelligence (AI).

7 Claims, 14 Drawing Sheets

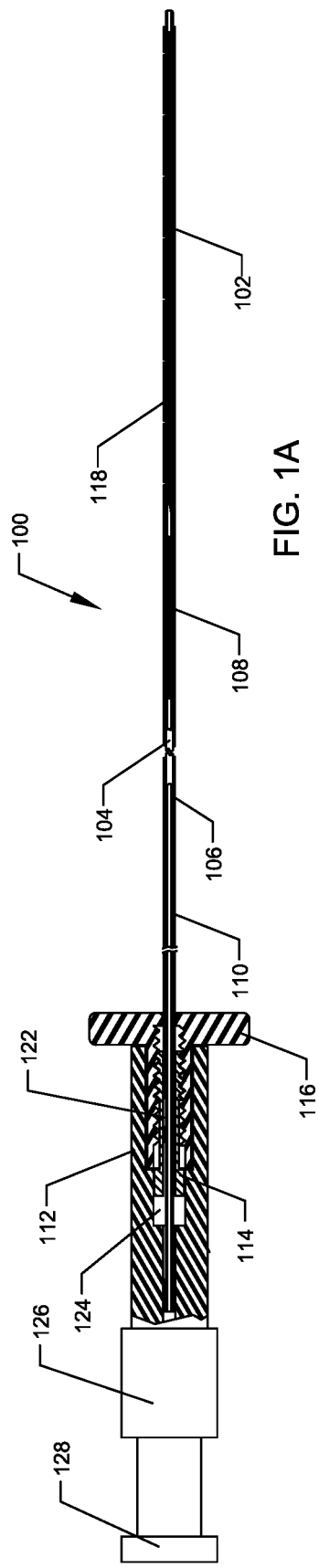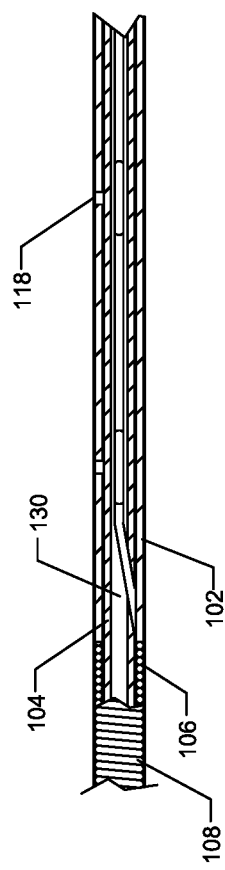

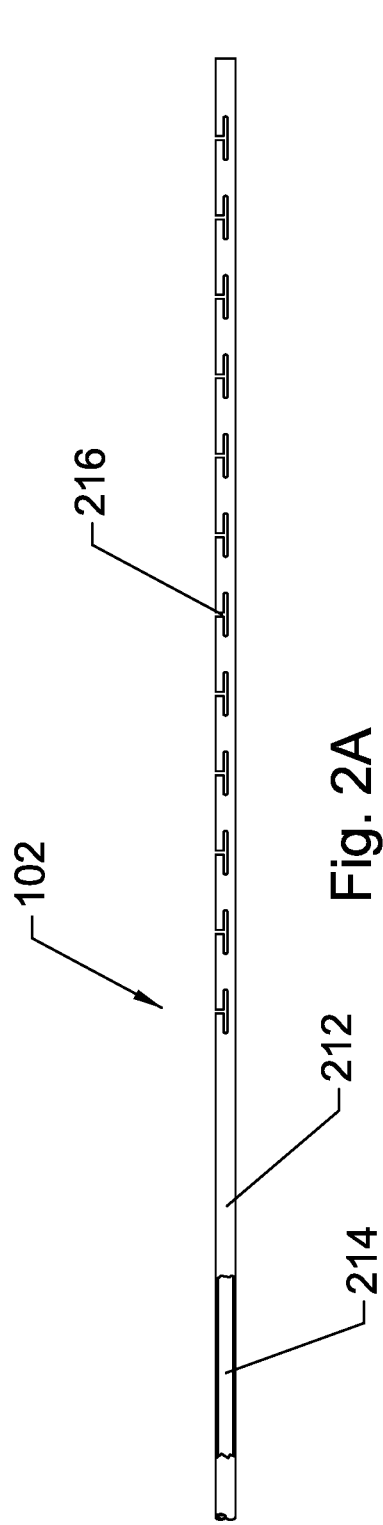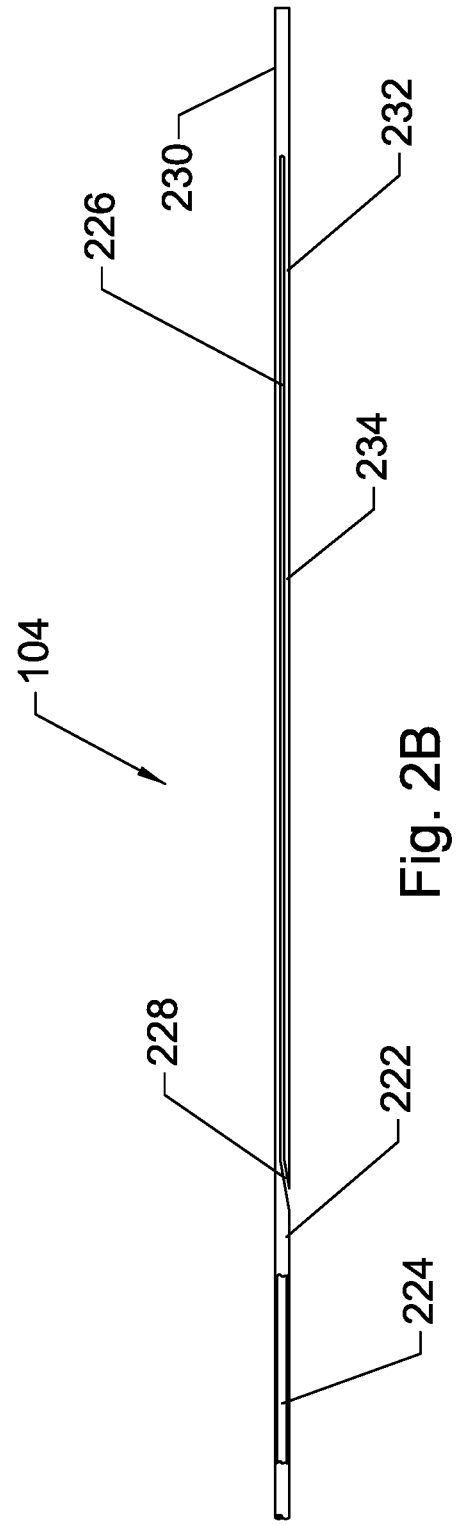

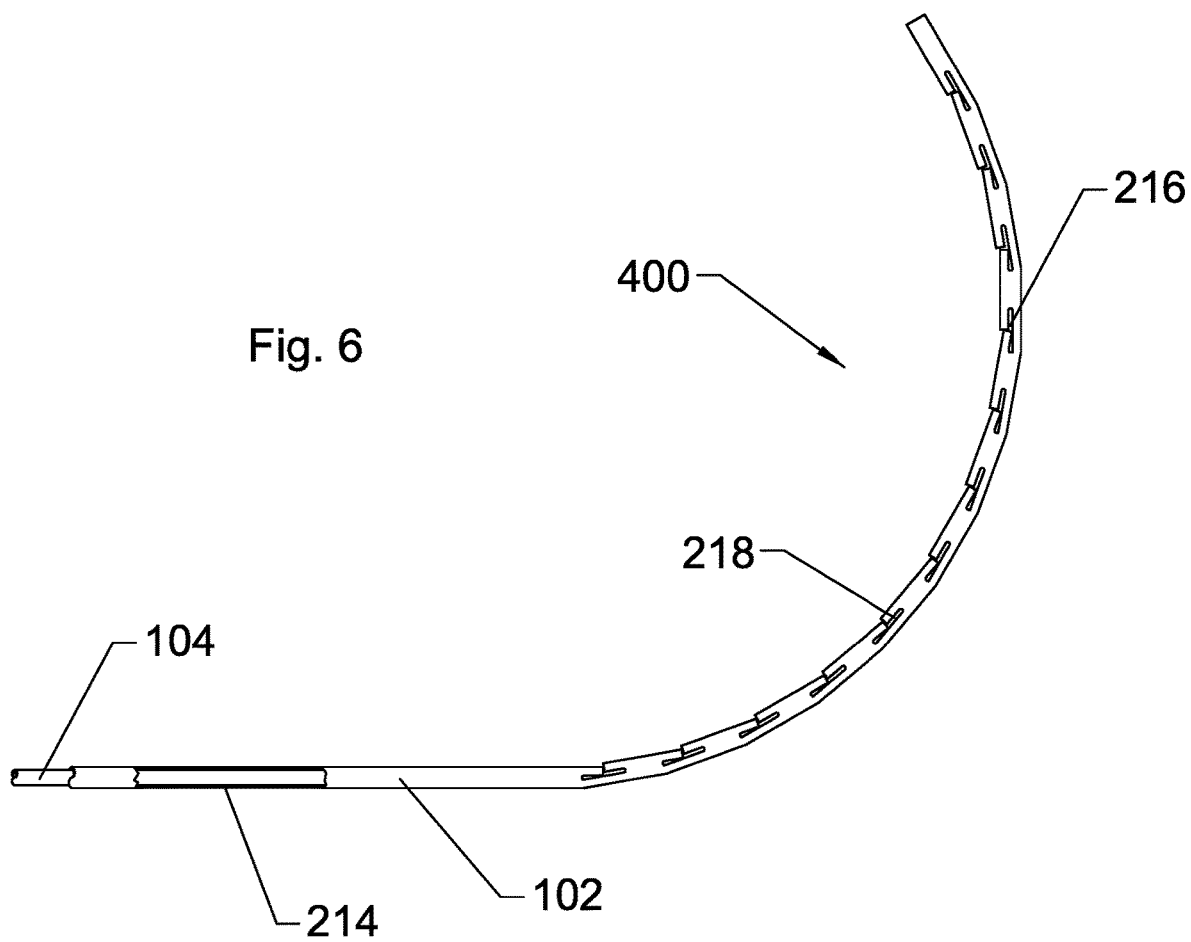

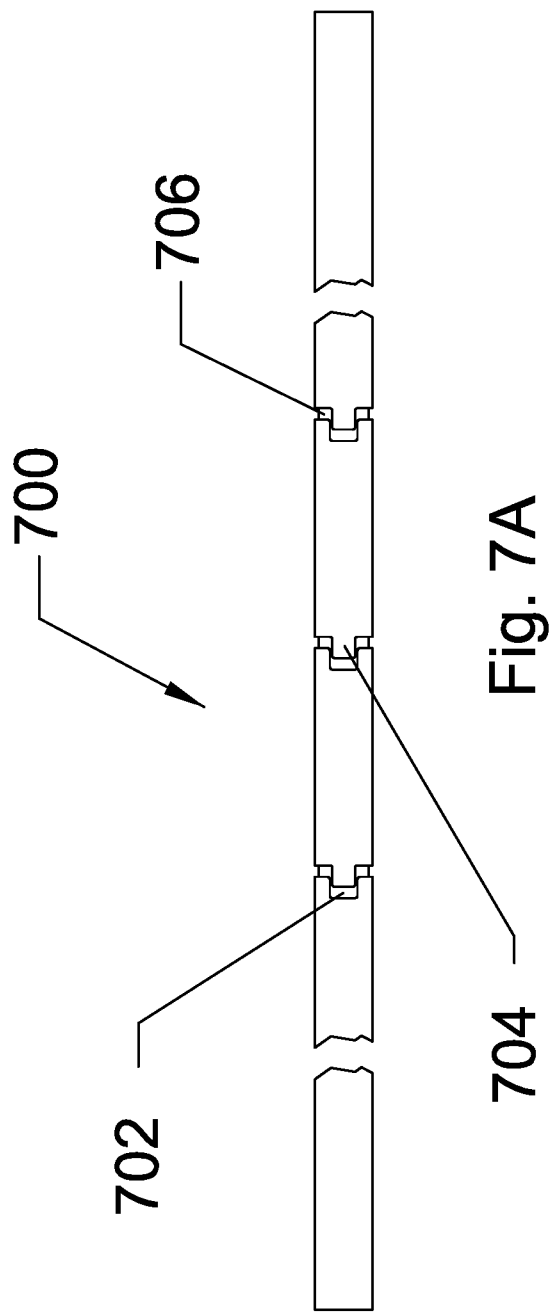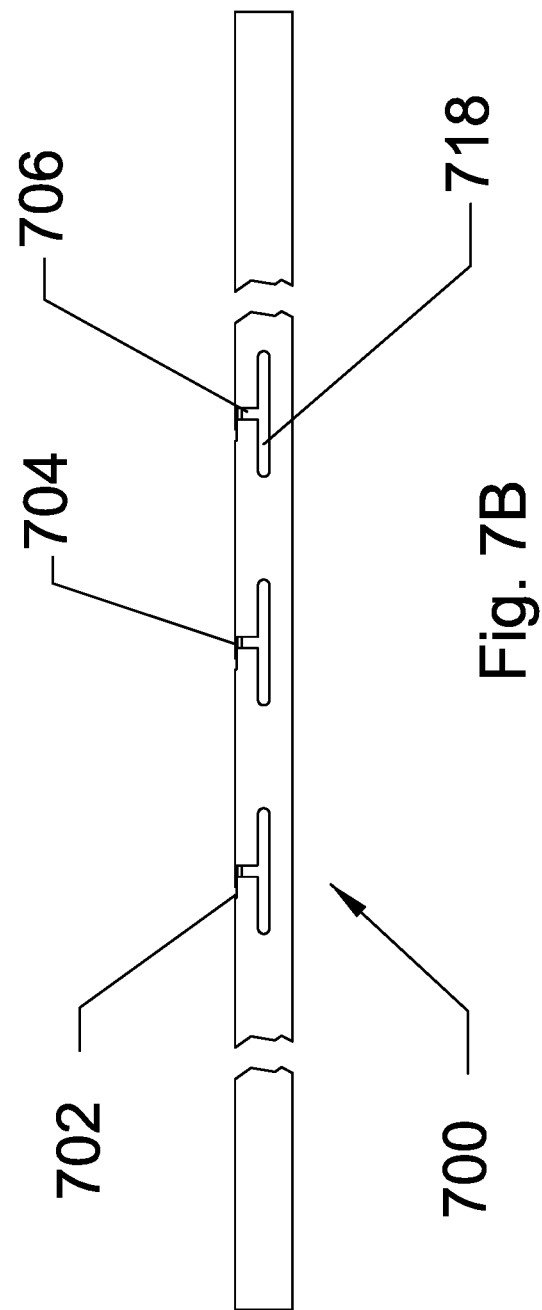

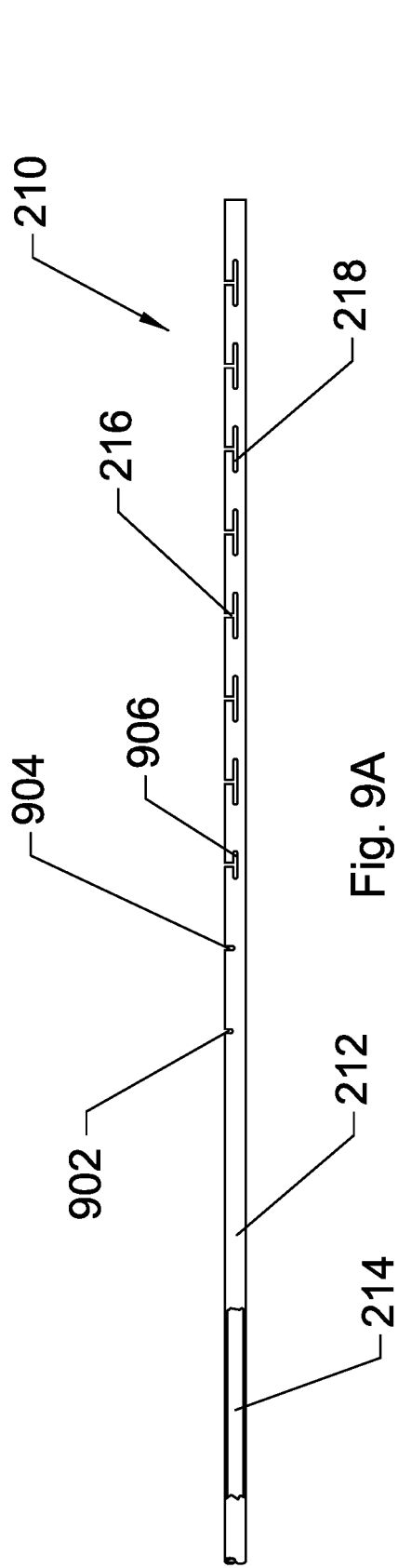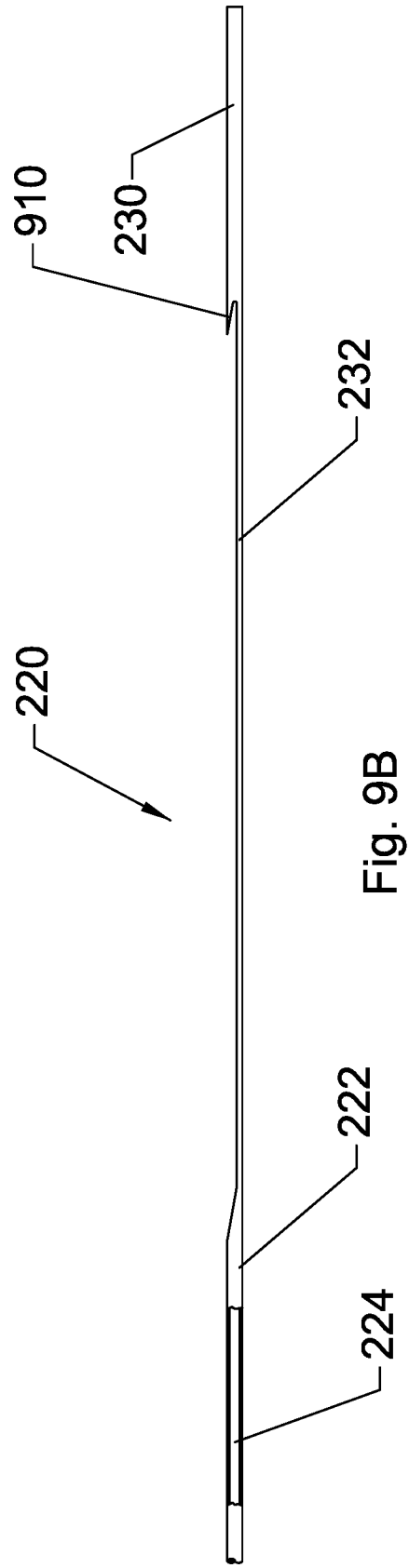

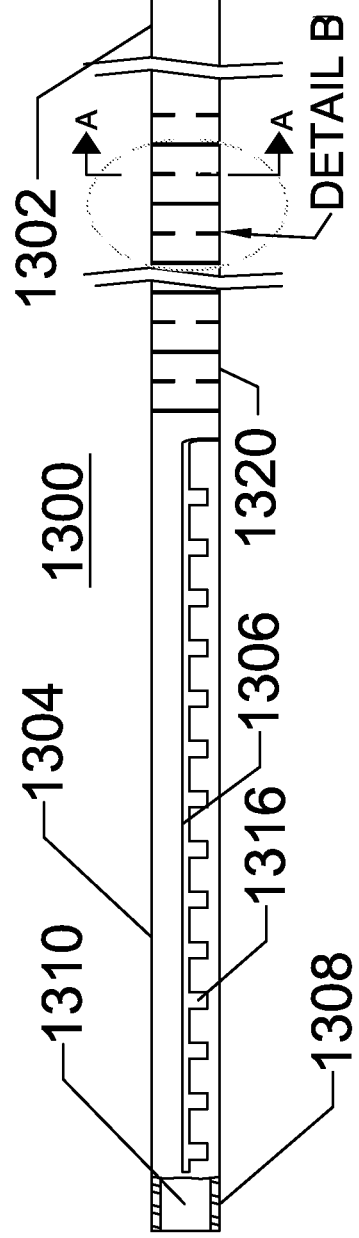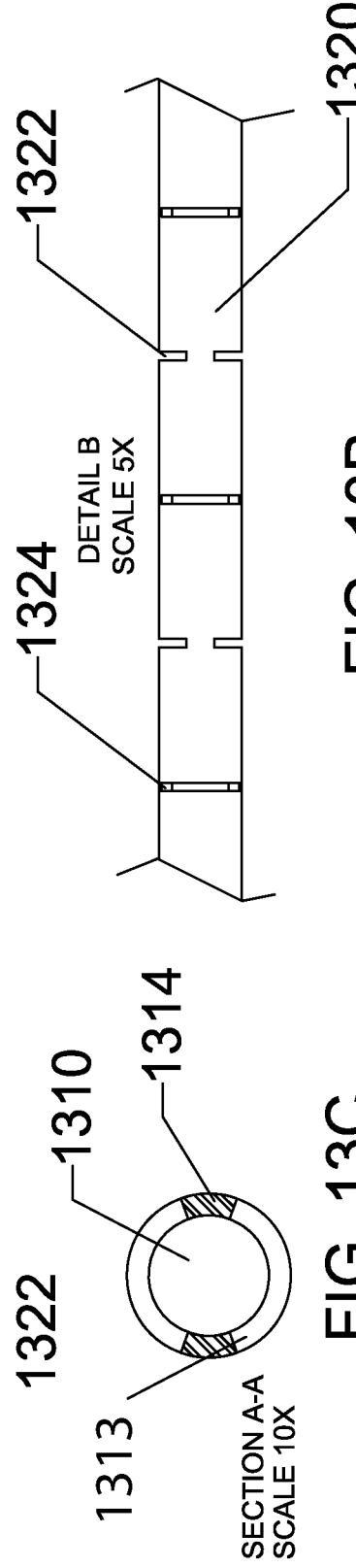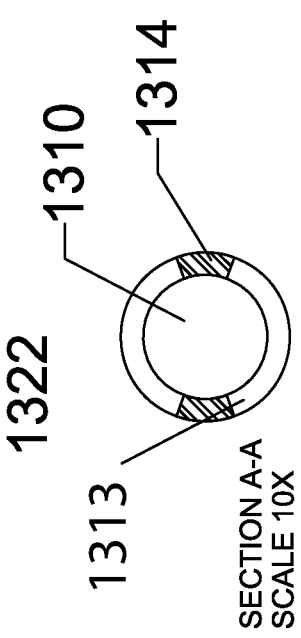

STEERABLE MICROCATHETER AND METHOD OF USE

FIELD OF THE INVENTIONS

The inventions relate to steerable microcatheters and methods for using microcatheters.

BACKGROUND OF THE INVENTIONS

During certain interventional procedures that are directed at cardiac access, the patient is catheterized through an access point in a vein or artery. A catheter is routed to the heart or other region of the cardiovascular system through the access point, which may be created by a cutdown or a percutaneous access procedure. The catheter may be routed to a target location within the heart, cerebrovasculature, or other region of the cardiovascular system. The routing is typically performed using a percutaneous access procedure, in some cases called a Seldinger procedure. In other vascular access procedures, open surgical access is required. In either case, a microcatheter is advanced into the vasculature by way of the percutaneous or open procedure. A guidewire can serve as a tracking system over which the microcatheter can be routed to a target site within the patient.

A guidewire can be routed through the vasculature, body lumens, vessels, in conjunction with a guide catheter, microcatheter, introducer, or other catheter to permit steering, additional support, or guidance, for the microcatheter, catheter or guide catheter.

SUMMARY OF THE INVENTIONS

The devices describe below include a microcatheter capable of articulating, steering, bending, deflecting, or otherwise being controlled off-axis to permit tracking within a vessel or body tissue, or moving to within a certain target location within a hollow organ. This articulation or steering can be performed in isolation, without interaction with any guidewires or other catheters, if desired.

The microcatheter may be routed through body tissue external to the vasculature or any other body vessels or ducts, if it is sufficiently rigid and retains column strength. In these embodiments, the microcatheter can comprise a central trocar, a sharp tip or cutting blade, a radiofrequency (RF) electrode, HIFU antenna, biopsy sampling window, cryogenic temperature emitter, or the like, to penetrate the tissue as the microcatheter is advanced. Microcatheters can be used for procedures such as transcatheter, endovascular, or vascular access as well as for transcutaneous, laparoscopic, thoracoscopic, and intramuscular access, and the like.

The steerability, deflection, or articulation, of a distal region of the microcatheter device can be accomplished using an inner tube and an outer tube, concentrically arranged and radially constrained together in the distal region of the microcatheter. The inner tube outer diameter is a close tolerance slip fit to the inside diameter of the outer tube but the inner tube is free to translate along a longitudinal axis of the tubes relative to the outer tube. Thus, only relative translational motion along the longitudinal axis is used to generate the articulation. The inner and outer tubes may be constrained so as not to move circumferentially with respect to each other. The inner tube can be modified in a region proximate the distal end such that the inner tube is divided, weakened, or split, into two or more parts along a generally longitudinal direction. Only a portion of these divided parts of the inner tube are affixed or integral, at their proximal end, to the more proximal portion of the inner tube. The parts of the inner tube not affixed, or integrally formed, at their proximal end can be optionally affixed or integral near their distal end to the portions of the inner tube that are also affixed at their proximal end. The divided portions of the inner tube, in the region of desired bending, form one or more control rod and one or more stay, or keeper, which serve to maintain the lumen as open as possible and hold the control rod or rods off center to maximize steering torque. The keeper, or stay, is disconnected from the rest of the inner tube at all but one axial location to allow maximum freedom of longitudinal movement relative to the control rod. The distal end of the inner tube can be formed as a helix or coil having a uniform, or variable, spacing between the coils or windings along one or more sides of the distal region.

The outer tube can be rendered flexible by cutting slots or gaps generally having a lateral or radial orientation, although there can be some projection at an angle or along the longitudinal axis of the outer tube. These lateral slots do not pass completely through the outer tubing such that the outer tubing is transected. Thus, a spine with ribs, having spacing between adjacent ribs, is formed in the outer tubing. The outer tube can be formed as a helix or a coil having a finite spacing between the coils or windings along one or more sides of the distal region. The outer tube can further comprise elastomeric webs between the coils. These webs can easily expand in tension but compression is more restricted. The webs can be disposed between the coils, exterior to the coils, or a combination thereof. The web can comprise materials such as, but not limited to, polyurethane, polyimide, silicone polyester, and the like. The web can provide for a fluid-right, leak-free-barrier to prevent fluids from escaping the lumen of the microcatheter into the surrounding or ambient space around the microcatheter. The expansion in tension can serve to allow the coil to travel around tight turns while the compression restriction can prevent substantial length reduction when the distal end of the entire system is placed in tension by proximal relative movement of, or force application by, the inner tube. The outer tube can be formed as a helix or coil having a variable spacing between the coils or windings along one or more sides of the distal region. One or more backbones or series of locking devices can optionally be added to prevent longitudinal compression, expansion, or both on one side of the winding or coil in this configuration. As used herein, the coil construction embodiment having one or more backbones or fixation columns is used interchangeably with embodiments where the distal part of the outer tube which is rendered flexible by way of a plurality of cuts, slots, or the like. A closed coil in the outer tube, with or without a backbone, can be used to prevent substantial compression but allow for tensile expansion in the longitudinal direction.

The inner tube can be affixed to the outer tube at a region distal to the lateral slots in the outer tube. The portion of the inner tube that is affixed or integral to the outer tube is that portion of the split inner tube that is connected or integral, at its proximal end, to the more proximal portions of the inner tube. The inner tube can be configured with an asymmetric distal end. The inner tube is preferably split along its length at the distal end. The split is oriented so that it radially migrates toward and through the side of the inner tube on one side, thus separating it into a leaf. This configuration leaves a connected side and a disconnected side to the inner tube. The disconnected side can be affixed to the connected side near the distal end by a bridge.

The inner tube can be a tube or it can be a solid core structure such as a round rod, square rod, C-shaped rod, or similar. Furthermore, a plurality of inner tubes can be radially nested to permit operable function of a plurality of control rods for steering, therapeutic manipulation, and the like in more than one axis.

Thus, articulation is generated using a plurality of (two or more) nested, radially constrained, substantially concentric axially translating tubes, wherein a first tube is weakened on one side to increase flexibility and limit final curvature and shape while a second tube is split substantially longitudinally and broken off on one side within the region where the first tube is also weakened. Both tubes may be substantially held in place to maintain hoop strength, column strength, kink resistance, and orientation of discreet structures, such as breaks or slots exist within the plurality of tubes. Axial forces applied to one tube relative to the other tube cause uneven stress to be applied to the distal end leading to overall tube bending off-axis.

The parts of the microcatheter, for example those parts disposed proximally to the bendable steering region, can comprise an outer tube that is of standard, unbroken cylindrical configuration with one or more intermediate tubes fabricated from cylindrical tubes of different bendability, cylindrical tubes having flexibility-enhancing slots cut therein, closed coils, braided windings, or coils being open between the windings or with variable openings between the windings. The proximal region, the inner tube can be affixed to a solid structure or a wire rather than a tube. Shaft stiffness can vary moving distally to proximally. The stiffness may increase continually, or in steps moving distal to proximal. Shaft diameter can vary with preferred embodiments comprising larger diameters in the more proximal regions.

The steerable microcatheter can be fabricated, to benefit, in outer diameters ranging from about 0.005 inches to about 0.200 inches, or larger. It may be beneficial to build these devices in outside diameters of 0.010 to 0.090 inches or larger. The length of a microcatheter can range from about 10-cm to about 250-cm or longer. Exemplary microcatheters can comprise an inner diameter of about 0.010 to 0.011 inches. An exemplary microcatheter can comprise an inner diameter of about 0.016 to 0.018 inches. The steerable microcatheter can be typically less than half as long as a guidewire over which is to be loaded so that the guidewire can remain gripped by the user at both its proximal and distal ends with the microcatheter fully inserted over the guidewire. A guidewire can be used in conjunction with the microcatheter to achieve some stability and maximize strength. For example, a guidewire with a curved tip can be withdrawn into a microcatheter to achieve a straight configuration, then be advanced outside the guide catheter into its curve and advanced into a vessel or body lumen, wherein the microcatheter is then advanced along the guidewire until the next steering event is required. The tip curving can be generated by articulation in situ of the microcatheter distal end, rather than pre-curving the structure.

Wall thicknesses can vary depending on strength requirements. For a 0.020-inch outside diameter microcatheter, for example, an overall, composite wall thickness of 0.005 inches or less can be achieved. The overall wall thickness of the composite structure can range down to 0.002 inches or less, especially for microcatheters having outside diameters of 0.010 to 0.015 inches or less. The composite wall can comprise the inner tube, the outer tube, the gap between the inner tube and the outer tube, an optional exterior covering and an optional inner liner. In larger microcatheters, for example those with outside diameters of 1 mm to 2 mm, or more, composite wall thicknesses of up to about 0.005 inches, or even greater, can be appropriate to maintain proper strength.

The inner tube or tubes, and the outer tube, can be fabricated from materials with high tensile strength such as, but not limited to stainless steel, cobalt nickel alloys, nitinol, polyether ether ketone (PEEK), polyimide, titanium, tungsten, or the like. External or internal layers can be added to provide for friction reduction and fluidic sealing since the catheter walls are perforated. Metals can preferably comprise spring hardness or even comprise superelasticity (pseudoelasticity), in the case of nitinol.

Retention of the inner lumen to the largest possible area is a primary, preferred goal. The inner lumen is the working channel through which therapies and diagnostics are delivered. Drugs and fluids can be infused through lumens, material withdrawn into the lumens from the patient, devices delivered of implanted, energy delivered, and the like. The inner lumen can comprise separation structures or walls that divide the microcatheter lumen into a plurality of lumens. Thus, these catheters can comprise one, two, three, or more lumens. The lumens typically extend from the proximal to the distal end of the microcatheter and can be operably connected go ports on the proximal end of the microcatheter.

The steerable microcatheter may be configured with a hub that is permanently attached or detachable, re-attachable, and able to provide deflecting control over the distal end, following re-attachment. The hub provides for grip by an operator or a robotic connection. The hub further comprises a control mechanism for the distal bending or steering. The hub can also comprise connectors and optional valves, for fluidic injection or removal, instrument passage, or the like.

A twist lock can be created at the hub end of the steerable microcatheter. Rotation of the twist lock can prevent relative movement of the inner tube relative to the outer tube. This twist lock can take the form of two rectangular or oval tube segments nested within each other. The inner tube is configured with a dimensional increase at its proximal end. By exposing the dimensionally increased part of the inner tube relative to the outer tube and twisting it to approximately 90 degrees from its nested orientation, the inner tube is prevented from moving within the outer tube. This apparatus can provide for one or more discreet locking location. The twist lock can be free to move or it can be spring loaded to control its circumferential position.

For purposes of summarizing the inventions, certain aspects, advantages and novel features of the inventions are described herein. It is to be understood that not necessarily all such advantages may be achieved in accordance with any particular embodiment of the inventions. Thus, for example, those skilled in the art will recognize that the inventions may be embodied or carried out in a manner that achieves one advantage or group of advantages as taught herein without necessarily achieving other advantages as may be taught or suggested herein. These and other objects and advantages of the present inventions will be more apparent from the following description taken in conjunction with the accompanying drawings.

BRIEF DESCRIPTION OF THE DRAWINGS

A general architecture that implements the various features of the inventions will now be described with reference to the drawings. The drawings and the associated descriptions are provided to illustrate embodiments of the inventions and not to limit the scope of the inventions. Throughout the drawings, reference numbers are re-used to indicate correspondence between referenced elements.

FIG. 1A illustrates a side, partial cutaway view of a steerable microcatheter having a hub, a proximal region, an intermediate region, and a steerable distal region;

FIG. 1B illustrates a magnified side, partial breakaway view of a transition between the distal steerable region and the intermediate region;

FIG. 2A illustrates a side, partial breakaway, view of an outer tube of a steerable microcatheter comprising a plurality of slots near the distal end to generate a region of increased flexibility in a preferential direction;

FIG. 2B illustrates a side, partial breakaway, view of an inner, tube of the steerable microcatheter comprising a longitudinal slot dividing the tube into two axially oriented parts which are connected at the distal end of the inner tube;

FIG. 6 illustrates a side view of the distal end of the steerable microcatheter incorporating the inner split tube and the outer slotted tube with the inner tube being pulled proximally relative to the outer tube causing the outer tube to deform into a curve;

FIG. 7A illustrates a top view of a portion of the distal flexible region of an outer tube comprising dovetails or interlocking grooves to reduce torque or side-to-side motion;

FIG. 7B illustrates a side view of a portion of a flexible region of an outer tube comprising dovetails or locking grooves to allow for torque transfer and maximize flexibility;

FIG. 9A illustrates an outer tube cut in its flexible regions with shorter lateral slots and with reduced or complete elimination of some T-slots to improve resistance to bending in that region;

FIG. 9B illustrates an inner tube wherein the disconnected side has been removed, leaving only the connected side and the distal end;

FIG. 13A illustrates a side view of an inner tube comprising a longitudinal slot in the region of steering, and a plurality of slots arranged in sequence to permit bending in more than one direction orthogonal to the longitudinal 1 axis;

FIG. 13B illustrates a magnified view of the bending region located proximal to the steering region, showing lateral cuts coming into the tube from different sides to permit bending in more than one direction;

FIG. 13C illustrates a magnified cross-sectional view showing the material removed during one of the lateral slot creation processes.

DETAILED DESCRIPTION OF THE INVENTIONS

Figure 3:
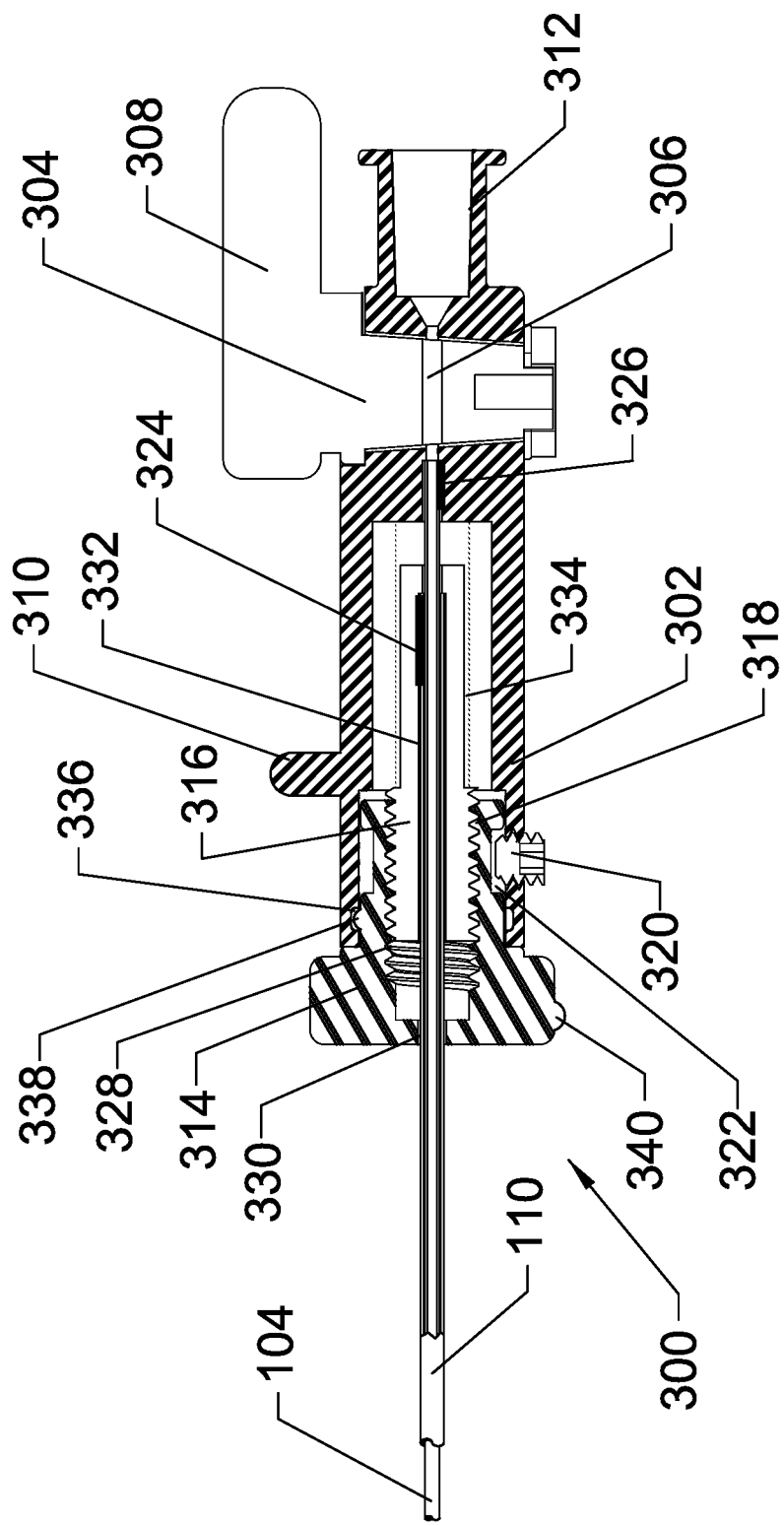
FIG. 3 illustrates a cross-sectional view of the proximal end of the steerable microcatheter comprising a stopcock and a bend adjusting mechanism.

In accordance with current terminology pertaining to medical devices, the proximal direction, or end, is defined herein as that direction, or end, on the device that is furthest from the patient and closest to the user, while the distal direction, or end, is that direction, or end, closest to the patient and furthest from the user. These directions and locations are applied along the longitudinal axis of the device, which is generally an axially elongate structure optionally having one or more lumens or channels extending through the proximal end to the distal end and running at least a portion of the length of the device. A catheter size given in the units of "French" or "Fr" is defined as three times the diameter in millimeters. Thus, a device that is 2 mm in diameter can be said to have a diameter of 6 French. Diameters can also be expressed in imperial units of inches.

In an embodiment, the inventions is an endoluminally, transvascularly, or endovascularly placed steerable microcatheter, with internal deflectability or the ability to articulate, at its distal end, in a direction away from its longitudinal axis. The steerable microcatheter is generally fabricated from stainless steel, nitinol, titanium, or the like and comprises an outer tube, an inner tube, a hub, and a distal articulating region. The deflecting or articulating mechanism is integral to the steerable microcatheter and component connections can rely on integral construction (1-piece), welds, bonds, connectors, or the like. The steerable microcatheter is useful for animals, including mammals and human patients and can be routed through body lumens or other body structures to reach its target destination. The steerable microcatheter can further comprise external polymeric sleeves, internal polymeric liners, exterior and interior coatings, and the like.

In an embodiment, the steerable microcatheter comprises at least an inner tube and an outer tube. The steerable microcatheter can also comprise a stylet or obturator, which can be removable or non-removable. The steerable microcatheter further comprises a hub at its proximal end which permits grasping of the steerable microcatheter as well as features, or control mechanisms, for controlling the articulation at the distal end. Such features can comprise control knobs, handles, levers, or the like. The proximal end further can optionally be terminated with one or more bayonet mounts or connectors, preferably female Luer or Luer lock ports or hemostasis valves, which can be suitable for attachment of pressure monitoring lines, dye injection lines, vacuum lines, a combination thereof, or the like. The steerable microcatheter can comprise a center lumen, channel, or channels, operably affixed to the Luer or Luer lock port, said channel being useful for dye injection, material or fluid administration or removal, pressure monitoring, implant delivery, or the like. In some embodiments, it is beneficial that another catheter be advanceable over the microcatheter beginning at the proximal end of the microcatheter.

The steerable microcatheter, or catheter, is fabricated so that it is, initially, substantially straight from its proximal end to its distal end. Manipulation of a control mechanism at the proximal end of the steerable microcatheter causes a distal region of the steerable microcatheter to bend or curve in a radial direction away from its longitudinal axis. The bending, steering, deflecting, or articulating region is located near the distal end of the steerable microcatheter and can be a flexible region or structure placed under tension or compression through control rods or tubular structures routed from the control handle at the proximal end of the steerable microcatheter to a point distal to the flexible region. The bending can be configured to occur in more than one region of the steerable catheter.

Other embodiments of the inventions comprise methods of use. One method of use involves inserting the central core wire or stylet so that it protrudes out the distal end of the steerable microcatheter. A percutaneous or cutdown procedure is performed to gain access to structures such as, but not limited to, the vasculature, either a vein, an artery, a body lumen or duct, a hollow organ, musculature, fascia, cutaneous tissue, the abdominal cavity, the thoracic cavity, and the like. A percutaneous access can involve placing an introducer, which can be a hollow, large diameter, hypodermic needle within the vasculature through a skin puncture. A guidewire (or the microcatheter itself, without the guidewire) can next be routed into the patient through the introducer. The introducer can be removed leaving the guidewire in place. The steerable microcatheter can be next inserted over the guidewire and into the patient. At this point, the guidewire can be removed, if desired. The microcatheter can be routed proximate to the target treatment site with the aid of its own internal steering mechanism to negotiate bifurcations, branch-vessels, and the like.

In an exemplary embodiment, a steerable microcatheter can be routed to a lesion in the cerebrovasculature by way of an entry point in a femoral artery. The steerable microcatheter can be routed cranially through the aorta and into a carotid artery. The steerable microcatheter can be routed through the carotid siphon, which is very tortuous, and on into the circle of Willis and adjacent vascular structures. Transit through the carotid siphon can be aided by prior placement of a floppy guide catheter, a guidewire, or both. Once routed to the target region in the cerebrovasculature, the distal tip can be articulated laterally. The degree of articulation and radius of curvature can vary. In an exemplary embodiment, the articulation occurs over a radius of about 3 to 4 mm and the degree of articulation approaches approximately 80 to 120 degrees. At this point, the distal end of the steerable microcatheter can reside within a cerebrovascular aneurysm that needs to be treated. An embolic coil can be deployed, for example using a pusher wire, from the distal end lumen of the microcatheter into the aneurysm. The embolic coil can be released from its pusher and left behind to form an implant to close off the aneurysm, either alone or in concert with additional coils or implants. A microcatheter with an internal lumen diameter of about 0.017 inches can be used to perform this type of procedure.

The steerable microcatheter can be adjusted so that it assumes a substantially straight configuration at any time. In other procedural embodiments, the steerable microcatheter can be advanced through the central lumen of an already placed catheter, sheath, introducer, or guide catheter. In other embodiments, the steerable microcatheter can be placed over an already placed guidewire, either standard or steerable. The steerable microcatheter comprises a generally atraumatic, non-sharp, distal tip. The distal tip can be rounded, oval, flattened, or the like. A central stylet wire, preferably removable, can be used to further blunt the distal end of the microcatheter.

In some embodiments, the steerable microcatheter is routed through the central lumen of an already placed guide catheter. The guide catheter can, in some embodiments, comprise extremely flexible structures that can conform to vascular anatomies that are quite tortuous. Such structures include the carotid siphon, located in the neck of a patient. The carotid siphon can comprise bends with radii of about 3-4 mm and the angle of articulation can reach to between 90 degrees and 180 degrees. This vessel can comprise a corkscrew shaped anatomy configured to allow the head to rotate from side to side and up and down. This vessel is the gateway to the circle of Willis and needs to be traversed to reach the majority of cerebrovascular vascular targets. The flexible guide catheter can be used to generate a liner within the carotid siphon thus allowing other devices, such as the steerable microcatheter to traverse the carotid siphon without potentially causing any damage to the vessel walls. Very flexible guide catheters, sometimes termed flow-directed catheters, can be advanced through the carotid siphon to provide this protection. Once the flow-directed guide catheter is placed, the steerable microcatheter can then be advanced therethrough and on into the distal cerebrovasculature.

In other embodiments, the steerable microcatheter can be configured to create a fenestration in a vessel wall. The steerable microcatheter can be configured to create a fenestration in a vessel wall, traverse soft tissue, and fenestrate and enter a second vessel. The steerable microcatheter can comprise a sharp tip, RF electrode, central cutting trocar, or the like. The steerable microcatheter can further be configured to deploy a shunt, stent, stent-graft, or the like which traverses between one vessel and another. The steerable microcatheter can comprise a balloon dilator at or near its distal end or at intermediate points. The steerable microcatheter can comprise a balloon expandable deployment mechanism for stents, stent grafts, shunts, and the like. In an exemplary embodiment, the steerable microcatheter can be configured to create the passageway and deploy an arteriovenous (AV) shunt, for example in the arm, the leg, or elsewhere in the body. Examples of AV shunts can include, but are not limited to, hepatic shunts for TIPS procedures, shunts in the legs to relieve hypertension, syncope, and the like, forearm shunts, injection shunts for drug delivery or dialysis, and the like.

The distal end of the steerable microcatheter, and optionally the body of the microcatheter as well, is sufficiently radiopaque that it is observable clearly under fluoroscopy or X-ray imaging. The steerable microcatheter, especially near its distal end, can be configured with symmetrical (for example rings or short hollow cylinders) or asymmetric radiopaque markers that provide some indication regarding the side of the steerable microcatheter that deflection can occur. The location of the steerable microcatheter and the amount of deflection and curvature of the distal end are observed and controlled using fluoroscopy or X-ray imaging, or other imaging method such as MRI, PET scan, ultrasound imaging, and the like. One or more radiopaque markers can be affixed to the distal end of the steerable microcatheter to enhance visibility under fluoroscopy. Such radiopaque markers can comprise materials such as, but not limited to, thick ferrous metals, tantalum, gold, platinum, tungsten, platinum iridium, and the like. Polymeric components of the steerable microcatheter can further be loaded with barium compounds, bismuth compounds, and the like.

Deflection of the distal tip to varying degrees of curvature, under control from the proximal end of the microcatheter can be performed. The curve can be oriented along the direction of a branching vessel or vessel curve so that the steerable microcatheter can then be advanced into the vessel by way of its high column strength and torquability. Alignment with any curvature of the catheter can be completed at this time. When correctly positioned under fluoroscopy, ultrasound, or other imaging system, dye can be injected into the central lumen of the steerable microcatheter at its proximal end and be expelled out of the distal end of the steerable microcatheter to provide for road-mapping, etc. This steering function can be very beneficial in device placement and is also especially useful in highly tortuous vessels or body lumens which may further include branching structures such as bifurcations, trifurcations, and the like.

In some embodiments, the inner tube, the outer tube, or both, can have slots imparted into their walls to impart controlled degrees of flexibility. The slots can be configured as "snake cuts" to form a series of ribs with one or more spines. The spines can be oriented at a given circumferential position on the outer tube, the inner tube, or both. The spines can also have non-constant orientations. In some embodiments, only the outer tube is slotted. In preferred embodiments, the backbone segments (or double backbone segments) can be configured to substantially restrict or prevent tube length compression or expansion (or both), but allow the inner tube to transmit longitudinal forces to the distal steering region without loss of flexibility in certain regions. The double backbone segments can be configured so as to symmetrically transmit forces longitudinally through the microcatheter. The slots can be generated within the distal portion of the outer tube where the curve is generated and these slots can be selectively oriented to provide a preferential bend direction. The slots and/or coils can also be generated within the distal portion of the outer tube where the curve is generated and these slots can be variable in nature to selectively have variable oriented flexibility in the preferential direction. This distance can range between about 0.5-cm and 15-cm of the end and preferably between 0.5-cm and 5-cm of the distal end. The slot widths can range between 0.0005 inches and 0.100 inches with a preferable width of 0.001 to 0.003 inches. In exemplary embodiments, the slot widths are about 0.0015 to 0.0060 inches. In some embodiments, it is desirable to have the outer tube bend in one direction only but not in the opposite direction and not in either lateral direction. In this embodiment, cuts can be made on one side of the outer tubing within, for example, the distal 10-cm of the tube length. Approximately 5 to 30 cuts can be generated with a width of approximately 0.0010 to 0.0060 inches. The cut depth, across the tube diameter from one side, can range between 10% and 90% of the tube diameter. In an embodiment, the cut depth can be approximately 40% to 60% of the tube diameter with a cut width of 0.025 inches. An intermediate cut can be generated on the opposite side of the tube. In an embodiment, the outer tube can be bent into an arc first and then have the slots generated such that when the tube is bent back toward the intermediate cuts, the tube will have an approximately straight configuration even through each tube segment between the cuts is slightly arced or curved. The number of these fenestrations in the tube wall can vary depending on required bendability. In some embodiments, the slots can be spaced between about 0.005 inches to about 0.025 inches or more. In more preferred embodiments, the slots can be spaced about 0.008 to 0.020 inches. In preferred embodiments, the slots are configured to allow the steerable microcatheter to traverse radii as small as 3 mm.

FIG. 1A illustrates a side view of a steerable microcatheter 100 comprising a distal outer tube 102, an inner control tube or rod 104, an outer low-friction coating 106, an exterior seal layer 118, an intermediate outer tube 108, a proximal outer tube 110, a hub body 112 further comprising a hub body lumen 124, a jackscrew traveler 114, a stopcock or hemostasis valve 126, an internal O-ring or seal (not shown), a fluid-tight connector 128, one or more interior lumens 130, and a control knob 116.

Referring to FIG. 1A, the distal end of the inner control tube or rod, hereafter called the inner tube, 104 is affixed to the distal end of the distal outer tube 102 using a weld, solder joint, adhesive bond, fastener, fixation device, or the like. The inner control tube or rod 104 is slidably disposed within the inner lumen of the distal outer tube 102 except at the distal end where they are affixed to each other. The proximal end of the distal outer tube 102 is affixed to the distal end of the intermediate outer tube 108 by integral formation, a weld, fixation device, adhesive bond, or the like. The proximal end of the intermediate outer tube 108 is affixed to the distal end of the proximal outer tube 110 by integral formation, a weld, fixation device, adhesive bond, or the like. The exterior of the outer tube can be covered with a fluid-tight seal 118, which can prevent fluid egress or ingress through the plurality of slots cut into the tubes. The fluid tight seal layer 118 can comprise materials such as, but not limited to, PET, PTFE, PFA, polyimide, polyurethane, and the like. The wall thickness of the fluid tight seal layer 118 can be about 0.0001 to about 0.0010 inches or more, with a preferred thickness of about 0.0002 to 0.0005 inches. The fluid-tight seal layer can, in preferred embodiments, comprise elastomeric materials that can stretch and compress in concert with the slots in the tubes opening and closing. Furthermore, the fluid-tight seal layer beneficially does not substantially droop or curve inside the slots, a situation that could restrict follow-on bending properties of the steerable microcatheter. The entire outer tube assembly 102, 108, 110, 118, can be covered with an optional anti-friction coating or layer 106. The coating 106 can comprise materials such as, but not limited to, a hydrophilic material such as hydrogel, silicone oil, or the like.

The microcatheter comprises one or more through lumens 130 to permit infusion of fluids therethrough or for advancement of a stylet (not shown) beyond the distal end of the microcatheter 100. The control knob 116 is rotationally free to move within the hub body 112, to which it is longitudinally affixed and the two components do not move axially relative to each other. The jackscrew traveler 114 can move axially within a lumen 124 within the hub body 112 within the constraints of the end of the internal lumen 124 of the hub body 112. The jackscrew traveler 114 is keyed within the lumen 124 by a non-round cross-section that impinges on complimentary structures within the hub lumen 124 to prevent relative rotational movement of the two components 112, 124. The jackscrew traveler 114 comprises external threads that are complimentary and fit within internal threads of the control knob 116. Thus, when the control knob 116 is turned, the jackscrew traveler 114 is forced to move axially either forward or backward because the control knob 116 is longitudinally affixed within the hub body 112.

A thread pitch for the jackscrew traveler 114 and the control knob 116 can range from about 5 to about 64 threads per inch (TPI) with a preferred range of about 10 TPI to about 48 TPI and a more preferred range of about 15 to about 36 TPI.

FIG. 1B illustrates a magnified, side cross-sectional view of the steerable microcatheter 100 of FIG. 1A at the transition between the distal end of the intermediate region 108 and the proximal end of the distal, steerable region. The steerable microcatheter 100 transition region comprises the intermediate outer tube 108, the distal outer tube 102, the inner tube 104, the central lumen 130, the fluid barrier 118, and the polymeric outer coating 106. In other embodiments, the fluid barrier 118 can comprise an inner tube or coating disposed on the interior of the innermost tube which then lines the lumen or lumens 130.

The polymeric outer coating 106 is optional but beneficial and can comprise materials such as, but not limited to, fluoropolymers such as PTFE, PFA, FEP, polyester (PET or PETG, polyamide, PEEK, and the like. The polymeric outer coating 106 can render the coiled embodiment of the intermediate outer tube 108, as illustrated, to retain a relatively smooth exterior surface and provide for friction reduction which is useful when passing a long, slender microcatheter through a long, catheter lumen. The distal outer tube 102 can be affixed to the intermediate outer tube 108 by means of a weld, fastener, adhesive bond, embedment with polymeric, metallic, or ceramic materials, or the like. The intermediate outer tube 108, illustrated in this embodiment as a coil structure with substantially no spacing between the coils, is highly flexible and the flexibility can be controlled by the elastic modulus, thickness, and other material properties of the outer coating 106. The intermediate outer tube 108, in other embodiments, can comprise structures such as, but not limited to, an unperforated or unfenestrated tube, a tube with partial lateral cuts, T-slots, H-slots, a spiral cut tube, a ribcage with a backbone, or the like.

FIG. 2A illustrates a side view, in partial breakaway, of the distal end of the axially elongate distal outer tube 102, comprising a lumen 214, a proximal, uncut portion 212, a plurality of lateral partial cuts 216, formed into longitudinal "T" or "H" cuts.

Referring to FIG. 2A, the distal outer tube 102 serves as the outer tube of the steerable microcatheter such as that illustrated in FIG. 1. The plurality of partial lateral cuts 216 serve to render the region of the outer tube 102 in which the lateral cuts 216 are located more flexible than the proximal region 212. The plurality of longitudinal "T" cuts (looking from a side), serve to further render the region of the outer tube 102, in which the "T" cuts reside, more flexible than in tubes where such "T" cuts 216 were not present. The longitudinal "T" cuts are optional but are beneficial in increasing the flexibility of the outer tube 102 in the selected bend region. The "T" cuts can also be described as "H" slots or just be laterally disposed slots or partial lateral slots. The longitudinal region comprising the slots 216 serve to distribute bending stress and reduce the possibility of structural yield during bending.

The partial lateral slots 216 can be spaced apart by about 0.005 to about 1.0 inches with a preferred range of about 0.008 inches to about 0.5 inches and a further preferred range of about 0.01 inches to about 0.025 inches. In an exemplary embodiment, the partial lateral slots 216 are spaced about 0.01 inches apart. The spacing between the partial lateral slots 216 can vary. In some embodiments, for example, the spacing between the partial lateral slots toward the proximal end of the outer tube 102 can be about 0.300 inches while those partial lateral slots 216 nearer the distal end of the outer tube 102 can be spaced about 0.150 inches apart. The spacing can change in a step function, it can change gradually moving from one end of the outer tube 102 to the other, or it can increase and decrease one or more times to generate certain specific flexibility characteristics. Increased spacing increases the minimum radius of curvature achievable by compression of the partial lateral slots 216 while decreased spacing allows for a smaller minimum radius of curvature.

The number of lateral cuts 216 can number between about four and about 5,000 with a preferred number being between about six and about 300 and a more preferred number of about eight to about 50. In the illustrated embodiment, there are 12 partial lateral cuts 216, all of which are modified using "T"-slot (they could be referred to as "H" slots depending on how you look at them) configurations. In other embodiments, the partial lateral cuts 216 can be shaped differently. For example, the partial lateral cuts 216 can be at angles other than 90 degrees to the longitudinal axis, curved, V-shaped, Z-shaped, W-shaped or the like. In other embodiments, the "T" slots 218 can have, for example, further cuts approximately lateral to the longitudinal axis, along any portion of the "T" cut.

The outer tube 102 can have an outer diameter of about 0.005 to about 0.250 inches with a preferred outside diameter of about 0.010 to about 0.100 inches and a more preferred diameter of about 0.015 inches to about 0.080 inches. In the illustrated embodiment, the outside diameter is about 0.048 inches while the inner diameter is about 0.036 inches. The inside diameter of the outer tube 102 can range from about 0.002 inches to about 0.240 inches for the diameters cited herein.

FIG. 2B illustrates an embodiment of a side view, in partial breakaway, of the distal end of an axially elongate inner tube 104, comprising a lumen 224, a proximal, uncut portion 222, a longitudinal slot 226 further comprising an angled lead in 228, a free side 234, a pusher or connected side 232, and a distal tip 230.

Referring to FIG. 2B, the distal tip 230 interconnects the free side 234 and the pusher side 232. The distal tip 230 or end of the inner tube 104 can further comprise a rounded, tapered, or blunted tip or nose cone (not shown). The disconnected free side 234 and the connected pusher side 232 are generally integrally formed but can also be affixed to each other by welding, adhesives, solder joints, fasteners, or the like.

The lead in 228 to the longitudinal slot 226 is beneficially angled to prevent other microcatheters, stylets, or other devices, which are inserted through the central lumen 224 from being caught or bumping against an edge. The angled lead in 228 serves a guide to assist with traverse of a stylet, obturator, or microcatheter past the lead in 228 and into the distal region of the steerable microcatheter. The lead in 228 can be angled from between about −80 degrees (the angle can be retrograde) from the longitudinal axis (fully lateral) to about +2 degrees and preferably from about +5 degrees to about +20 degrees with a most preferred angle of about +8 degrees and about +15 degrees. In the illustrated embodiment, the angle of the lead in slot 228 is about 10 degrees from the longitudinal axis. A second feature of the lead in 228 is that it be positioned or located proximally to the most proximal "T" slot 218 in the outer tube 102 when the two tubes 102, 104 are affixed to each other (see FIG. 9). The lead in 228 is located at least 1-cm proximal to the proximal most "T" slot 218 and preferably at least 2-cm proximal to the proximal most "T" slot 218 so that bending in the distal region does not distort the lead in 228 and cause kinking, misalignment, or pinching of the internal lumen 224.

The inner or intermediate tube 104 can have an outside diameter that is slightly smaller than the inside diameter of the outer tube 102 so that the intermediate tube 104 can be constrained to move longitudinally or axially within the outer tube 102 in a smooth fashion with relatively little force exerted. In the illustrated embodiment, the outside diameter of the intermediate tube 104 is about 0.033 inches giving about a 0.0015 inch radial clearance between the two tubes 102 and 104. The inside diameter of the intermediate tube 104 can range from about 0.006 to about 0.015 inches less than the outside diameter of the intermediate tube 104. In the illustrated embodiment, the wall thickness of the intermediate tube is about 0.006 inches so the inside diameter of the intermediate tube is about 0.021 inches. The lumen 224 of the intermediate tube 104 can be sized to slidably accept a removable or non-removable stylet or obturator 140 (not shown). A typical stylet wire 140 can range in diameter from about 0.01 to about 0.23 inches with a preferred diameter range of about 0.012 to about 0.020 inches. In another embodiment, the outer tube 102 has an outside diameter of about 0.050 inches and an inside diameter of about 0.038 inches. In this embodiment, the inner tube 104 has an outside diameter of about 0.036 inches and an inside diameter of about 0.023 inches. The radial wall clearance between the inner tube 102 and the outer tube 104 is about 0.001 inches and the diametric clearance is about 0.002 inches. The annulus between the two tubes must be substantially smooth, free from burrs, and free from contamination because the two tubes 102, 104 beneficially need to translate along their longitudinal axis relative to each other over relatively long axial distances of about 50 to about 150-cm.

The inner tube 104 transmits force along its proximal, stiffer, non-slotted region 222 from the proximal end of the inner tube 104 to the lead in 228 where the force continues to be propagated along the connected side 232 to the distal end 230. The outer tube 102 transmits force along its proximal non-slotted region 212. Longitudinal forces applied to the distal, flexible region with the slots 216 cause deformation of the outer tube in an asymmetrical fashion with the side of the outer tube 102 comprising the partial lateral slots 216 forming an outer curve if the slots 216 are expanded and an inside curve if the slots 216 are compressed. Forces to cause bending are preferably exerted such that the partial lateral slots 216 are compressed up to the point where the gap closes, but no further, however forces can also be exerted to expand the slots 216, however limits on curvature are not in place because the lateral slots 216 can open in an unrestrained fashion except for the material properties of the outer tube 102.

The disconnected side 234 of the inner tube 104, separated from the connected side 232 by the longitudinal slot 226 and the lead in 228, serves to maintain an undistorted tube geometry and provide resistance to deformation while helping to maintain the inner lumen 224 in a round configuration and provide a shoehorn or funnel effect to guide an obturator, microcatheter, or stylet 140 therethrough as they are advanced distally. The disconnected side 234, being separated from the force transmitting member 222 cannot provide any substantial longitudinal load bearing structure, although at its distal end, where it is integral or affixed to the distal end 230, some tension load carrying capability exists. The intermediate tube 104 can be considered a split tube and does not carry a load in compression or tension along substantially the entire length of the disconnected side 234. A main advantage of keeping the disconnected side 234 is to maintain the off-center positioning of the force transmitting member 222.

The partial lateral slot (or "T" slot) 216 in the outer tube 102 in the outer tube 102, as well as the longitudinal slot 226 in the inner or intermediate tube 104, and the lead in slot 228 can be fabricated by methods such as, but not limited to, electron discharge machining (EDM), wire EDM, photo chemical etching, etching, laser cutting, conventional milling, or the like. In other embodiments, different slot configurations can also be employed, such as curved slots, complex slots, zig-zag slots, or the like. In some embodiments, the partial lateral slot 216 can be configured with a tongue and groove or dovetail design to prevent or minimize lateral movement or torqueing of the outer tube 102 in the flexible region. In some embodiments, the tongue and groove or dovetail (not shown) can be generally centered between two "T" slots, for example. The parts can be ganged and fixture such that, using wire EDM, for example, a plurality of tubes can be cut to reduce manufacturing costs. As many as 20 to 30 tubes, or more, can be fixtured, secured, and etched by the aforementioned methods.

FIG. 3 illustrates a side, cross-sectional view of an embodiment of a hub end 300 of a steerable microcatheter. The hub end 300 comprises the outer proximal tube 110, the intermediate tube 104, a hub body 302 further comprising an integral stopcock body, a stopcock petcock 304 further comprising a petcock handle 308 and a petcock through bore 306, a Luer lock fitting 312, a keyed lumen 334, a setscrew or pin 320, a jackscrew body 316 further comprising a plurality of threads 328 and a central lumen 332, a control knob 314 further comprising a plurality of threads 318, a central lumen 330, the protrusion 338, and a circumferential recess 322, an outer tube weld 324, an orientation mark 340, and an intermediate tube weld 326. The hub body 302 can further comprise a plurality of recesses or complementary structures 336. The hub 300 can also comprise an arrow pointer 310 to assist in orientation of the direction of curvature at the distal end of the steerable microcatheter by reference points on the hub 300. In other embodiments, the hub can comprise gauges, audio output systems, visual output systems, or other mechanisms (not shown) to provide feedback as to the amount of articulation being imposed on the distal end of the microcatheter.

Referring to FIG. 3, the petcock 304 is affixed to the petcock handle 308 by welding, integral fabrication, fasteners, adhesives, or the like. The petcock 304 is retained within a lateral through bore in the hub body 302, which is in the illustrated embodiment, tapered, using a locking "C" washer, fastener, screw, pin, or the like (not shown). The stopcock body (not shown) can also be separate from the hub body 302 and be affixed thereto by welding, bonding, fasteners, and the like. The petcock 304 can be rotated about its longitudinal axis to align the through bore 306 with the axis and central lumen of the hub body 302 or it can be rotated sideways to shut off and seal the lumen against the flow of fluids. The Luer lock 312 can be affixed to, or integrally fabricated with, the hub body 302. The knob 314 is retained within the hub body 302 by the setscrew of pin 320 which prevents axial movement but permits rotational movement as constrained by the setscrew, projection, or pin 320 riding within the circumferential recess 322 which is integrally formed or affixed to the knob 314. The jackscrew body 316 is capable of axial movement within the hub body 302 but is restrained from rotation about the long axis by flats or features on the exterior of the jackscrew body 316 which are constrained by flats or features in the keyed lumen 334. The knob 314 comprises threads 328 on its internal lumen which engage with external threads 318 on the jackscrew body 316. Rotation of the knob 314 thus causes the jackscrew body 316 to move axially proximally or distally with mechanical advantage. Rotation of the knob 314 can be forced using manual action or using a motor or other mechanism (not shown). The proximal outer tube 110 can be affixed to the jackscrew body 316 by the outer tube weld 324. The inner tube 104 (which can also be called the intermediate tube) is affixed to the hub body 302 by the intermediate tube weld 326. The central lumen 224 of the inner tube 104 is operably connected to a central lumen of the hub body 302, the petcock through bore 306, and the lumen of the Luer fitting 312.

The knob 314 can comprise markings 340 to permit the user to visualize its rotary or circumferential position with respect to the hub body 302. These markings 340 can comprise structures such as, but not limited to, printed alphanumeric characters (not shown), a plurality of geometric shapes such as dots, squares, arrows, or the like, or the markings can comprise raised or depressed (embossed) characters of similar configuration as described for the printed markings. In an embodiment, the knob 314 can comprise a number on each of the facets so the facets can be numbered from one to 6, in the illustrated embodiment. The knob markings 340 can further comprise raised structures, as illustrated, which can further be enhanced with contrasting colors for easy visualization. The number of facets can range from about three to about 100.

The knob 314 can further comprise one or more complementary structures affixed or integral thereto, such as a plurality of protrusions 338 that fit into detents 336 affixed or integral to the proximal end of the hub body 302. Such protrusions extending into detents in the hub body 302 can provide a ratcheting or clicking sound as well as providing resistance to inadvertent movement of the knob 314 once it is rotated to the correct location. The knob 314, in some embodiments, can be biased toward the hub body 302 to ensure that complementary structures such as the protrusions and detents come into correct contact. In other embodiments, the knob 314 can comprise a ratchet system to further control its rotary movement with respect to the hub body 302. In other embodiments, the knob 314 can comprise one or more detents (not shown) while the hub body 302 can comprise one or more complementary protrusions (not shown). It is beneficial that the knob 314 be moved only when required by the user and not by accident or not when it is required to maintain its rotary position and, by consequence, the curvature at the distal end of the tubing. The number of ratchet locations, or low energy positions or setpoints, can range from about 2 per 360 degree rotation to about 20 with a preferred number of ratchet locations ranging from about 4 to about 12.

The hub body 302 can be fabricated from biocompatible metals such as, but not limited to, stainless steel, titanium, nickel coated brass, cobalt nickel alloy, and the like, although it could also be fabricated from polymeric materials in a less expensive format. In the polymeric materials embodiment for the hub, the outer tube can be affixed to a jackscrew, which is trapped longitudinally and rotationally within the hub body 302, and the inner tube can be affixed to an anchor, which is embedded into the hub body 302. The knob 314 can be fabricated from the same metals as the hub body 302 but it can beneficially be fabricated from biocompatible polymers such as, but not limited to, polyamide, polyimide, polyvinyl chloride (PVC), acrylonitrile butadiene styrene (ABS), acetal polymers, polycarbonate, polysulfone, PEEK, Hytrel®, Pebax®, and the like. The petcock 304 and petcock handle 308 can be fabricated from the same materials as the knob 314, or it can be different materials.

The jackscrew body (or traveler) 316 can be fabricated from the same materials as the hub body 302, or from different materials, but must be able to be strongly affixed to the outer tube 102.

The arrow pointer 310 can be affixed, or integral, to the hub body 302 or other component. The arrow pointer 310 is used to indicate the direction of bending or deflection at the distal end of the steerable microcatheter by reference points on the hub but due to torsional effects on such a long device as a microcatheter, the primary guide for orientation will be the fluoroscopic or X-Ray images taken of the distal end of the steerable microcatheter, in vivo. The hub system 300 illustrated in FIG. 3 is not detachable or releasable from the proximal end tubes 110 and 104. In other embodiments such as that of FIG. 1, the hub system 300 can be made to slide onto the tubes 110, 104 and clamp by means of locking mechanisms. In yet other embodiments, the hub 300 can be made to split open along its axis and then re-close and latch over the proximal ends of the tubes 110, 104.

Figure 4:
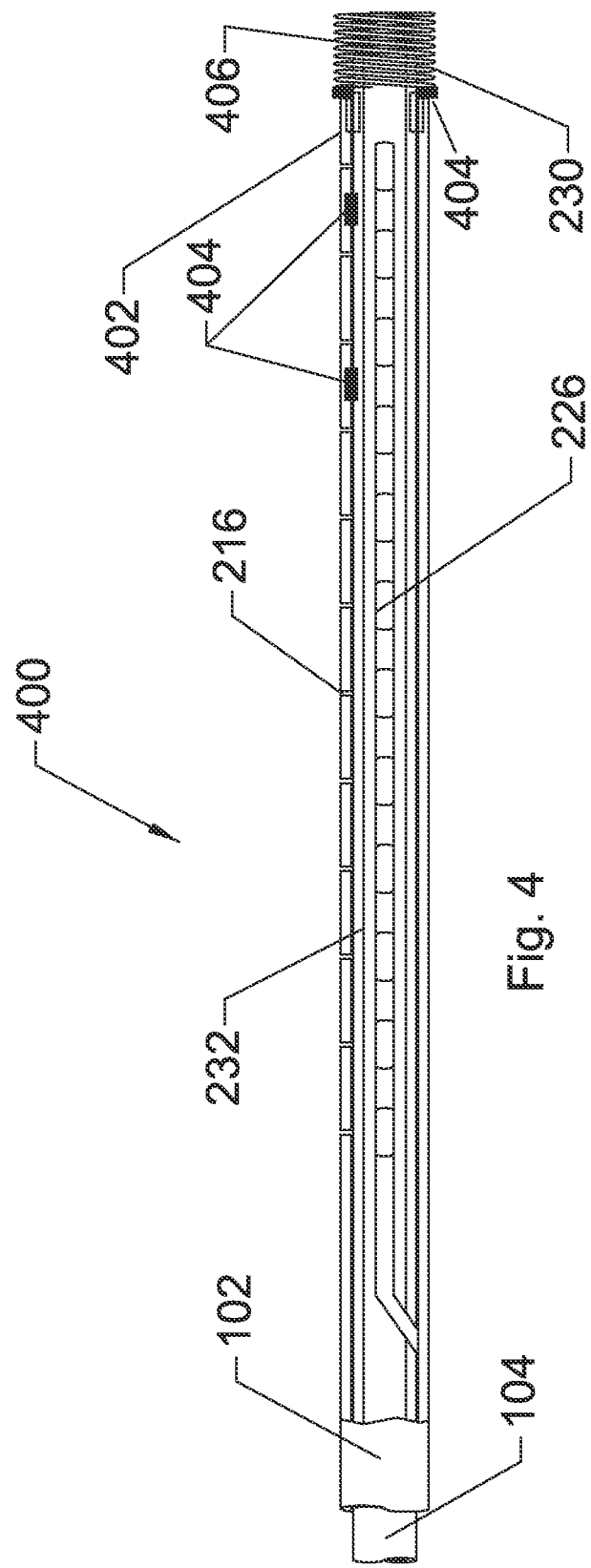
FIG. 4 illustrates a partial breakaway view of the distal end of the steerable microcatheter comprising the outer tube and the inner tube arranged concentrically and oriented circumferentially.

FIG. 4 illustrates a side view, in partial breakaway, of an embodiment of a distal end 400 of a steerable microcatheter. The distal end 400 comprises the distal outer tubing 102 further comprising the lateral partial slits 216 and the intermediate (or inner) tubing 104 further comprising the longitudinal slit 226 and the distal inner tube tip 230. A weld 402 affixes the distal end of the outer tubing 102 to the connected side 232 of the intermediate tubing. The distal end 400 can further comprise one or more separate radiopaque markers 404, which may or may not comprise a central lumen. The distal end can also comprise a tip coil 406 to reduce any chance of trauma caused by advancing the distal end against tissue. The tip coil 406 can be affixed to the distal tip 230 by swaging, adhesives, welding, connectors, or the like. The tip coil 406 can comprise regular coil pattern or a variable coil pattern. In a preferred embodiment, the most distal part of coil 406 can comprise wider coil spacing than the more proximal part.

Referring to FIG. 4, distal outer tube 102 and the inner tubing 104 are rotated about the longitudinal axis such that the connected side 232 of the inner tube 104 is generally aligned with, and affixed or welded 402 to, the distal outer tubing 102 on the side comprising the partial lateral slits 216. The width of the partial lateral slits, T-slots, H-slots 216, and the longitudinal slot 226 can range from about 0.001 to about 0.050 inches with a preferred range of about 0.001 to about 0.010 inches and more preferably from about 0.0015 to about 0.005 inches. In the illustrated embodiment, the slits 216, and 226 are about 0.010 inches. The width of the partial lateral slits 216 on the outer tube 102 can be used, in compression to provide at least some limit to how much the distal outer tube 102 can bend in compression along the side comprising the partial lateral slits 216. Note that the inner tube 104 may extend beyond the distal end of the distal outer tube 102. In the illustrated embodiment, the inner tube 104 extends about 5-mm to about 20 mm beyond the distal end of the distal outer tube 102. This construction provides for reduced device complexity, increased reliability of operation, and reduced manufacturing costs relative to other steerable devices. The steerable microcatheter, in the embodiments presented herein, has high column strength, and resistance to torque.

The distal end 400 of the steerable microcatheter can be generally fabricated from metals with sufficient radiopacity or radio-denseness that they are clearly visible under fluoroscopic or X-ray imaging. However, if this is not the case, additional radiopaque markers 404 can be affixed to the outer tube 102, the inner tube 104, or both. These radiopaque markers 404 can comprise materials such as, but not limited to, tantalum, gold, platinum, platinum iridium, barium or bismuth compounds, or the like. The radiopaque markers 404 can be beneficially oriented in an asymmetrical manner, as illustrated, to denote the direction of bending to an observer viewing an X-ray image of the distal end 400. The tip coil 406 can comprise materials such as, but not limited to, nitinol, stainless steel, tantalum, platinum, platinum iridium, and the like. The tip coil 406 can thus function as a radiopaque marker as well as an atraumatic distal end feature.

Close tolerances between the internal diameter of the outer tube 102 and the outside diameter of the inner tube 104, ranging from a radial gap of between about 0.0005 inches to about 0.008 inches, depending on diameter cause the two tubes 102 and 104 to work together to remain substantially round in cross-section and not be ovalized, bent, kinked, or otherwise deformed. This is especially important in the flexible distal region comprising the partial lateral cuts 216 on the distal outer tube 102 and the longitudinal slot 226 in the inner or inner tube 104. The two tubes 102 and 104 can be fabricated from the same materials or the materials can be different for each tube 102, 104. Materials suitable for tube fabrication include, but are not limited to, stainless steel, nitinol, cobalt nickel alloy, titanium, and the like. Certain very stiff polymers may also be suitable for fabricating the tubes 102, 104 including, but not limited to, polyester, polyimide, polyamide, polyether ether ketone (PEEK), and the like. The relationship between the inner tube 104, the distal outer tube 102, and the slots 216, 226, 228 serve to allow flexibility and shaping in high modulus materials such as those listed above, which are not normally suitable for flexibility. The internal and external surface finishes on these tubes 102, 104 are preferably polished or very smooth to reduce sliding friction between the two tubes 102, 104 because of their very small cross-sections and their relatively long lengths. Lubricants such as, but not limited to, silicone oil, hydrophilic hydrogels, hydrophilic polyurethane materials, PFA, FEP, or polytetrafluoroethylene (PTFE) coatings can be applied to the inner diameter of the distal outer tube 102, the outer diameter of the inner tube 104, or both, to decrease sliding friction to facilitate longitudinal relative travel between the two tubes which is necessary for articulating the flexible, slotted region near the distal end 400 of the articulating, deflectable, or steerable microcatheter. The exterior surface of the distal outer tube 102 can be covered with a polymeric layer, either substantially elastomeric or not, which can cover the slots 216, etc. and present a smoother exterior surface to the environment as well as optionally maintaining a closed fluid path through the lumen of the microcatheter. The exterior surface can be affixed or configured to slip or slide over the exterior of the outer tube 102.

The weld 402 affixes the distal outer tube 102 to the intermediate or inner tube 104 such that they cannot move relative to each other along the longitudinal axis at that point. However, since the two tubes 102, 104 are affixed to each other on the side of the distal outer tube 102 containing the partial lateral slots or gaps 216, compression or expansion of those gaps 216 can be accomplished by moving the weld 402 by relative movement of the inner tube 104 and the outer tube 102. The weld transmits the force being carried by the connected side 232 of the inner or intermediate tube 104 to the slotted side of the distal outer tube 102. Note that the terms intermediate tube 104 and inner tube 104 are used interchangeably, by definition. The inner tube 104 becomes an intermediate tube 104 if another tube, wire, stylet, or catheter is passed through its internal lumen 224.

In other embodiments, since the inner or intermediate tube 104 is split 226 lengthwise in the flexible region, a portion, or the entirety, of the distal end of the inner tube 104 can be affixed, adhered, welded, fastened, or otherwise attached to the distal outer tube 102 and functionality can be retained. The distal end 230 of the inner tube 104 can, in some embodiments be retained so as to create a cylindrical distal region 230 in the inner tube 104 and this entire cylindrical distal region 230, or a portion thereof that does not project distally of the distal end of the outer tube 102 can be welded to the outer tube 102 around a portion, or the entirety of the circumference of the outer tube 102. If only a portion of the inner tube 104 is welded to the distal outer tube 102, then the weld is beneficially located, approximately centered, on the side of the distal outer tube 102 comprising the partial lateral slots 216. The cylindrical distal region 230 is a beneficial construction, rather than completely cutting the inner tube 104 away on one side, since the distal region 230 projects distally of the distal end of the distal outer tube 102 to form the tip of the steerable microcatheter further comprising an atraumatic distal end. The tip coil 406 can be affixed to the distal outer tube 102, the distal end 230 of the inner tube 104, or both, using methodology such as, but not limited to, fasteners, welds, adhesive bonding, and the like.

In some embodiments, one of the welds, all of the welds, or a portion of the welds can be completed using techniques such as, but not limited to, TIG welding, laser welding, silver soldering, fasteners, adhesives, plasma welding, resistance welding, interlocking members, or a combination thereof. Laser welding is beneficial because it is highly focused and can be located with high accuracy. These welds include the weld 402 at the distal end that connects the inner tube 104 and the distal outer tube 102 as well as the welds at the proximal end connecting the inner tube 104 to the hub and the distal outer tube 102 to the traveler of the jack-screw 316.

Figure 5:
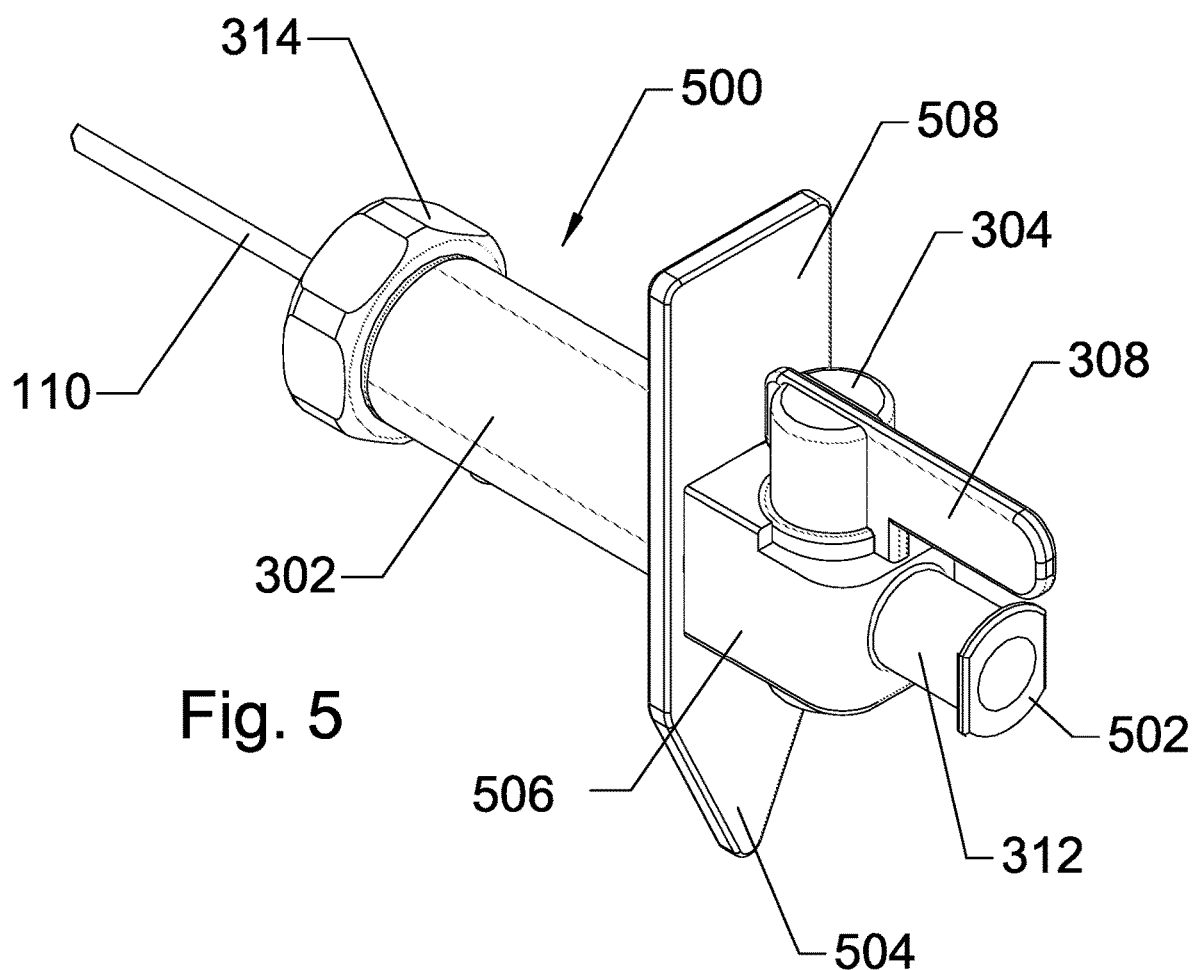
FIG. 5 illustrates an oblique view of the proximal end of the steerable microcatheter.

FIG. 5 illustrates an oblique external view of an embodiment of the proximal end 500 of the steerable microcatheter comprising the outer tube 110, the knob 314, the hub body 302, the arrow pointer 508 further comprising the pointed end 504, a stopcock body 506, the petcock 304, the petcock handle 308, and the Luer fitting 312 further comprising a locking flange 502. In this embodiment, the hub can be configured to be removable or it can be configured to be permanently affixed to the proximal end of the outer proximal tubing 110 and the inner tubing 104 (not shown).

Referring to FIG. 5, the pointed end 504 of the arrow pointer 508 can be integrally formed with the arrow pointer 508, or it can be affixed thereto. The arrow pointer 508, which is optional, can be integrally formed with the hub body 302, or it can be affixed thereto using fasteners, welds, adhesives, brazing, soldering, or the like. The stopcock body 506 can be integrally formed with the hub body 302 or it can be affixed thereto using fasteners, welding, soldering, brazing, adhesives, threads, bayonet mounts, or the like. Referring to FIGS. 3 and 5, the lumen of the Luer fitting 312 is operably connected to the through bore of the petcock 304 if the petcock 304 is aligned therewith (as illustrated), or the petcock 304 can be rotated about an axis to misalign the through bore of the petcock 304 with the Luer fitting 312 and prevent fluid flow or passage of solid material therethrough. The knob 314 can be round, shaped as a lever, it can comprise knurls, facets (as illustrated), or it can comprise a plurality of projections which facilitate grabbing and rotation by the user. Circumferential motion of the knob 314 about is longitudinal axis is preferably and beneficially smooth but with sufficient friction to maintain its position in any desired configuration.

FIG. 6 illustrates an embodiment of the distal end 400 of the steerable microcatheter in a curved configuration. The distal end 400 comprises the distal outer tube 102, the inner tube 104, the outer tube lumen 214, the plurality of outer tube longitudinal cuts or slots 218, and the plurality of outer tube partial lateral cuts 216.

Referring to FIG. 6, the outer tube partial lateral cuts 216 represent spaces that close up when the side of the tube in which the lateral cuts 216 are located is placed in compression. Such compression is generated by pushing the outer tube 102 distally relative to the inner tube 104. When the partial lateral cuts 216 gaps close, further compression is much more difficult because the outer tube 102 stiffens substantially when no further gap exists for compression. The composite structure, with the intermediate tube 104 nested concentrically inside the outer tube 102 is relatively stiff and resistant to kinking no matter what amount of curvature is being generated.

Preferred radius of curvatures for the distal end can range from about 0.20 inch to about 6 inches, with a preferred range of about 0.25 inches to about 2 inches and a more preferred range of about 0.3 to about 1.5 inches. The radius of curvature need not be constant. In some embodiments, the proximal end of the flexible region can have the partial lateral cuts 216 spaced more widely than those at the distal end of the flexible region, causing the distal end to bend into a tighter radius than, the proximal end of the flexible region. In other embodiments, the distal region can be less flexible than the proximal end of the flexible region.

The partial lateral cuts 216, and the "T"-slots in the outer tube 102 are beneficially treated using etching, electropolishing, passivation, sanding, deburring, machining, or other process to round the external edges of the partial lateral cuts 216. Thus, the edges are blunted or rounded so they are not sharp such as to cause the steerable microcatheter to dig, skive, or shave material from the inside of a catheter, dilator, or obturator.

FIG. 7A illustrates a top view of another embodiment of an outer tube 700 in the region of the distal, flexible section, wherein the outer tube 700 comprises a plurality of partial lateral cuts or slots 706 further comprising a dovetail 702. The dovetail 702 creates a groove 702 and further comprises a peg or projection 704 that rides or is circumferentially constrained within the groove 702 as long as the outer tube 700 is neutrally forced, or forced in compression on the side of the partial lateral cuts or slots 706. The projection 704 riding within the dovetail groove 702 provides for torque resistance and torsional rigidity in the area of the dovetail 702.

FIG. 7B illustrates a side view of the outer tube 700 in the region of the distal, flexible section, wherein the outer tube 700 comprises the partial lateral slots 706, the dovetail 702 further comprising the projection 704, and the "T" slots 218. The T-slots 218 are optional or they can be configured differently.

The steerable microcatheter can be used in the cardiovascular system, cerebrovascular system, the pulmonary system, the gastrointestinal system, or any other system comprising tubular lumens, where minimally invasive access is beneficial. The steerable microcatheter of the present inventions is integral and steerable. It is configured to be used with other catheters or guidewires that may or may not be steerable, but the steerable microcatheter disclosed herein does not require external steerable catheters or catheters with steerability to be steerable as it is steerable or articulating on its own. The steerable microcatheter is capable of bending and unbending a practically unlimited number of times. The steerable microcatheter is especially useful with catheters that are not steerable since the steerable microcatheter comprises its own steering system.

The steerable microcatheter can be removed from the lumen of a catheter following completion of its task. Without removal of the steerable microcatheter, the lumen is compromised and the capacity of the sheath to introduce catheters is reduced, given a certain outside diameter. This device is intended for use with catheters and is not intended for use as integral to a catheter. The steerable microcatheter device steers itself and can steer a catheter but is not a replacement for a steerable catheter.

The steering mechanism disclosed herein can be used to steer other types of catheters, guide catheters, introducers, sheaths, guidewires, punches, needles, or even obturators that are placed within the aforementioned devices, with high degree of control over long lengths up to 250 cm or more while requiring less wall thickness and thus allowing for larger internal lumens than steerable devices of the prior art with the same outside diameter. Typical sheaths can have internal lumens with capacities of, for example, 3-Fr to 12-Fr and still maintain very thin walls of around 1-Fr. While smaller catheters or guide catheters with lumens in the range of about 2-Fr to 5-Fr can have even smaller wall thicknesses, depending on the materials used to construct the walls of the sheath. Some sheath constructions can comprise composite materials such as an inner tube fabricated from metal and an outer tube fabricated from metal with a polymeric exterior coating. The inner tube can further be coated with an interior liner of, for example PTFE, or other fluoropolymers (PFA, FEP), Parylene, Pebax®, Hytrel®, polyimide, polyamide, PET, or the like, to create certain reduced frictional properties, electrically insulating properties, or both. These coatings or liners can range in thickness from about 0.0001 to about 0.005 inches, with a preferred thickness range of about 0.0005 to 0.002 inches.

The steering mechanism disclosed herein, comprising two or more nested axially elongate cylindrical tubes moving relative to each other only along the longitudinal axis, can provide a high degree of precision, repeatability, force, column strength, torsional control, and the like, in a configuration with extremely thin walls and large inside diameter (ID) to outside diameter (OD) ratio. One of the tubes comprises partial lateral cuts or complex lateral gaps and the other tube comprising a split running substantially the length of the flexible region. The disconnected side of the slit tube can be removed so that only a partially formed, connected side remains. However, in preferred embodiments, the disconnected side, which is actually retained at the distal end, is not removed but serves to fill space within the lumen of the outer tube 102 to prevent kinking, improve column strength, prevent lumen collapse and provide for guiding of central stylets or catheters. Prior art devices require greater wall thickness, which reduces the size of the internal lumen relative to a given outside diameter, or they do not have the same degree of precise movement at the distal tip under control from the proximal end of the device.

Figure 8:
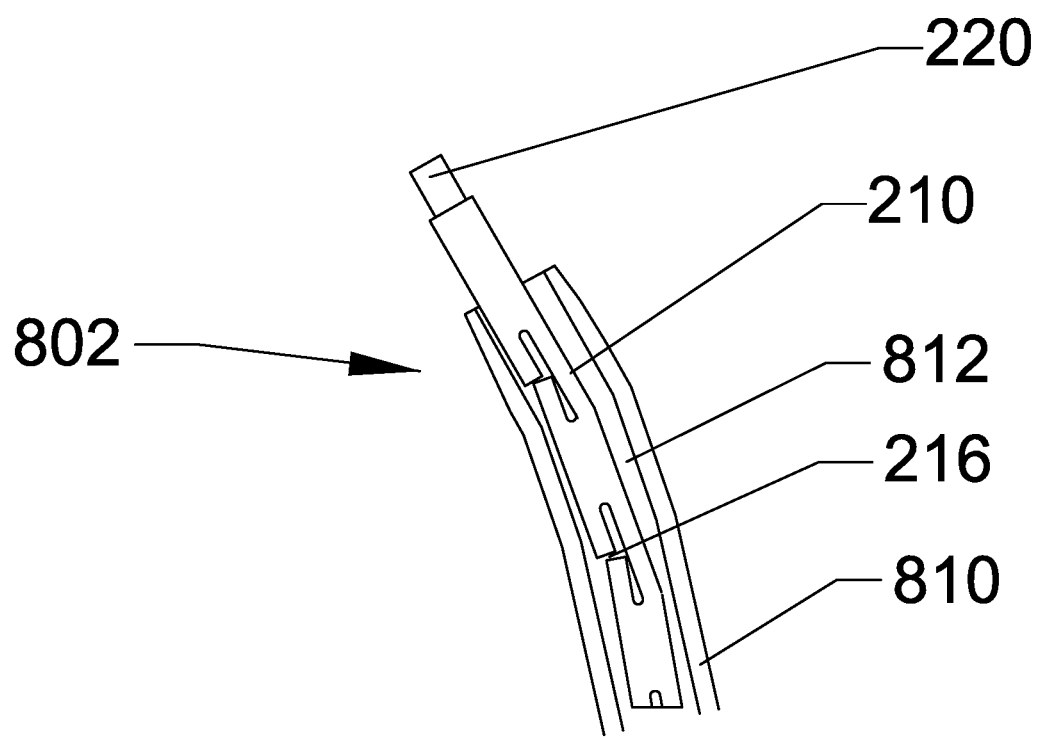
FIG. 8 illustrates the distal end of a steerable microcatheter being advanced through central lumen of a guide catheter or sheath.

FIG. 8 illustrates a side view of the distal end 400 the steerable microcatheter advanced through a central lumen 812 of a dilator or obturator 810 of a guide catheter 814 (not shown). The steerable microcatheter distal end 400 comprises the outer tube 102, comprising the plurality of partial lateral cuts 216, and the inner tube 104, comprising a distal end 220. The distal end 220 comprises, or is terminated by a rounded, blunted, atraumatic distal end 806. The steerable microcatheter 400 can further comprises a central lumen (not shown).

In some embodiments, the outer tube 102 can be modified to adjust stiffness. It can be preferential to increase the resistance to bending moving distally to proximally on the outer tube 102. This increase in bending resistance contravenes the tendency of the outer tube to bend more severely at the proximal end of the flexible region than in the distal region. It is possible to configure the bending so that the bend radius is approximately constant or such that a greater curvature (smaller radius of bending) is generated moving toward the distal end of the bendable region. The partial lateral slots 216 can be cut with reduced depth more proximally to increase the resistance to bending imparted by the outer tube 102. The partial lateral slots 216 can be cut more narrowly in the more proximal regions to reduce the distance the slot 216 can close. The T-slots 218 can be reduced in length or removed in the more proximal regions of the flexible region of the outer tube 102. Elastomeric bumpers or fillers can be added to some of the partial lateral slots 216 to reduce the amount the partial lateral slots 216 can compress. Once the partial lateral slots 216, associated with the T-slots 218 have closed under bending of the outer tube 102, further bending is resisted and is substantially arrested. By tailoring the width and spacing of the partial lateral slots 216, a specific final curvature can be tailored for a given catheter.

FIG. 9A illustrates the outer tube 102 comprising the lumen 214, the proximal tube wall 212, the plurality of partial lateral slots 216, the plurality of T-slots 218, a short partial lateral slot 902, a slightly longer partial lateral slot 904, and a standard length lateral slot 216 but with a shortened T-slot 906.

Referring to FIG. 9A, the most proximal partial lateral slot 902 penetrates less than the standard partial lateral slots 216. The second (moving distally) partial lateral slot 904 is slightly longer than slot 902 and therefore is more flexible in that region and requires less force to generate bending. The third partial lateral slot comprises the shortened T-slot 906 which reduces the ability of the tubing to bend given a constant bending force. The T-Slot 218 is a modification of the partial lateral slot 216 which comprises a substantially axial component of the slotting, which serves to reduce localized bending stress and an associated reduced risk of yield.

FIG. 9B illustrates the inner tube 104 comprising the lumen 224, the proximal region 222, the connected side 232, the distal end 230, and a beveled lead-in 910 at the proximal end of the distal end 230.

Referring to FIG. 9B, the proximal end of the disconnected region can be moved distally to increase the stiffness of the inner tube 104 in a specific region, generally the most proximal part of this distal, flexible region.

Figure 10A:
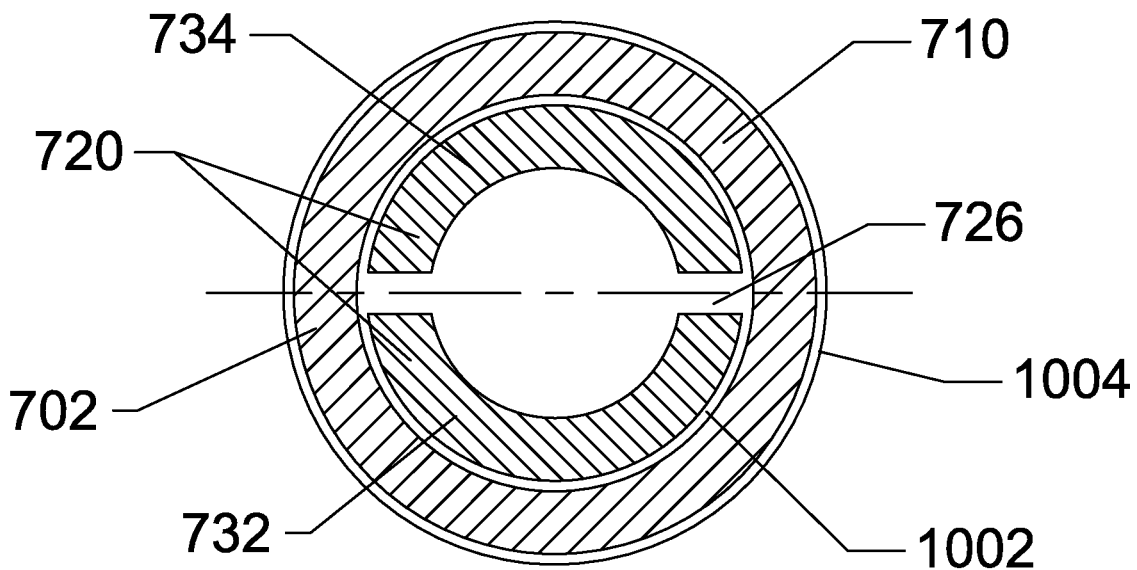
FIG. 10A illustrates a cross-sectional view of a tubing configuration in a steerable microcatheter within the flexible region, wherein the separation slot in the inner tube is substantially at the midpoint or center of the inner tubing.

In certain preferred embodiments, it is beneficial that the inner tube 104 can sustain compression to generate bending of the outer tube 102 at the distal end back to straight after being curved and even to bend beyond straight in the other (or opposite) direction. In order to sustain compression, it is beneficial that the disconnected side 234 be separated from the connected side 232 at or near substantially the center or midpoint of the tubing. Depending on the width of the slot 226 separating the disconnected side 234 from the connected side 232, the location of the slot can be offset from the midpoint but this is dependent on the wall thickness of the inner tube 104 and the angle of the slotting. In a preferred embodiment, interference exists between the disconnected side 234 and the connected side 232 such that the disconnected side and force transmitting member cannot move substantially inward, a situation that would have negative effects of obstructing the lumen, restricting fluid flow therethrough, trapping stylets or other catheters that need to move longitudinally therein, or buckling sufficiently to prevent application of longitudinal compression forces on the connected side 232. FIG. 10A illustrates a lateral cross-sectional view an inner tube 104 nested inside an outer tube 102 and separated from the outer tube 104 by a radial gap 1002 in the flexible region of a steerable microcatheter wherein the inner tube 104 is separated by a split or gap 226 into two approximately or substantially equal parts, a connected side 232 and a disconnected side 234, approximately (or substantially) at the midline or centerline of the cross-section.

Figure 10B:
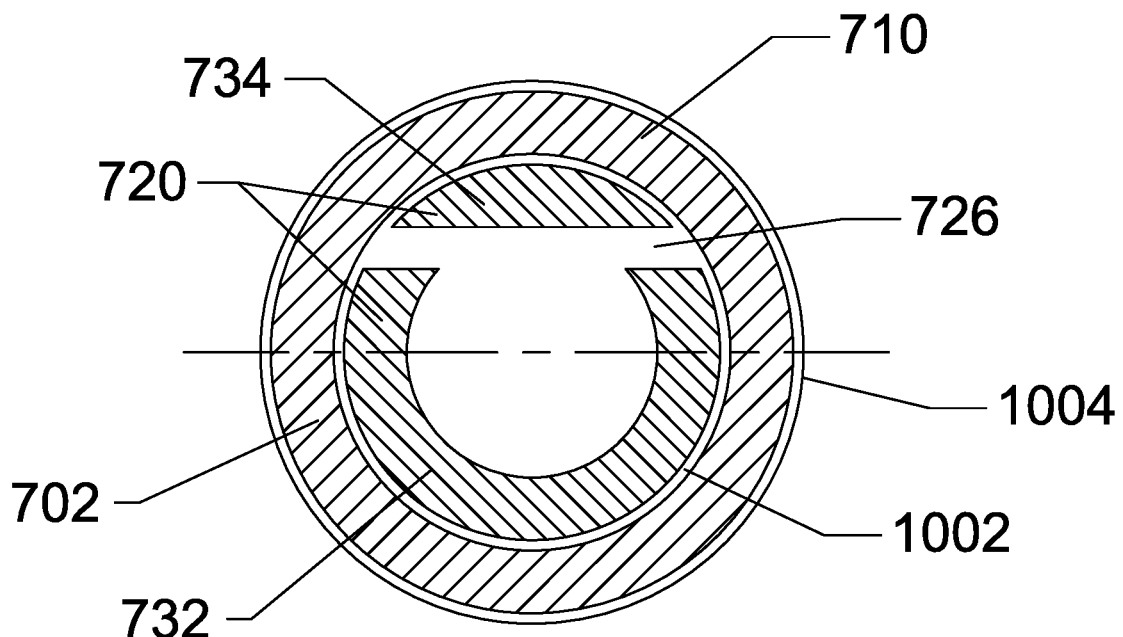
FIG. 10B illustrates a lateral cross-section of a tubing configuration of a steerable microcatheter within the flexible distal region, with an off-center slot.

FIG. 10B illustrates a lateral cross-sectional view an inner tube 104 nested inside an outer tube 102 and separated from the outer tube 104 by a radial gap 1002 in the flexible region of a steerable microcatheter wherein the inner tube 104 is separated by a split or gap 226 into two substantially unequal parts, a connected side 232 and a disconnected side 234, substantially offset from the midline or centerline of the cross-section.

Referring to FIGS. 10A and 10B, the disconnected side 734 is retained in close proximity to the outer tube 702 by its stiffness and its inability to deform such that the edges of the disconnected side 734 can pass beyond the edges of the connected side 732 and thus the two sides 732 and 734 are retained radially displaced from centerline. If the gap 726 were too large or either side 732, 734 were small enough to fit within the edges of the other side, then displacement of one side toward the centerline and confounding of the off-center orientation of the connected side 732 or 734 would occur leading to buckling of the connected side 732 in compression and inability to straighten out a bent steerable microcatheter. Another problem might be loss of torquability and predictability of the direction of bending. Both embodiments shown in FIGS. 10A and 10B maintain circumferential and radial orientation of the inner tube connected side 732 relative to the disconnected side 734 and promote high precision deflection of the distal tip. The structures illustrated in FIGS. 10A and 10B are preferably configured with a minimum area moment of inertia in the bending direction while maintaining sufficient cross section as to allow for steering, pushability and torquability.

In preferred embodiments, the radial gap 1002 is minimized and is retained between about 0.0005 to 0.002 inches when the steerable microcatheter is about 0.035 inches in outside diameter. Furthermore, the split or gap 726 should be as minimal as possible and in preferred embodiments can range from about 0.0005 inches to about 0.003 inches with a gap of about 0.0005 to 0.02 inches being most preferable.

Figure 11:
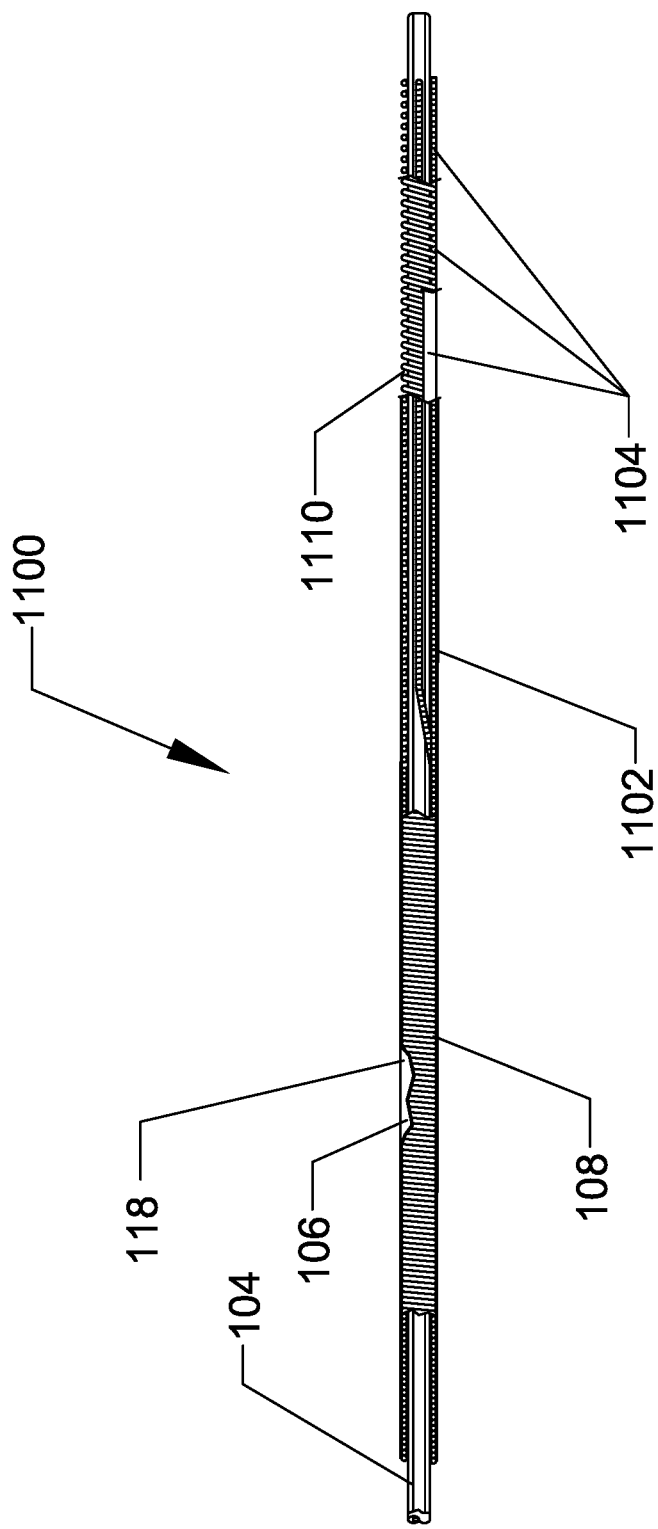
FIG. 11 illustrates a side, partial cutaway view of the distal end of a steerable microcatheter wherein the outer tube comprises a coil or helix with a small amount of space between the windings.

FIG. 11 illustrates a side, partial breakaway view of the distal end of a steerable microcatheter 1100 as well as a portion of the intermediate region. The steerable microcatheter 1100 comprises the inner tube 104, the coiled intermediate outer tube 108, the distal outer coil 1102, the backbone 1104, the polymeric outer coating 106, and the distal coil spaces 1110.

The polymeric outer coating 106 can extend the entire length of the steerable microcatheter 1100 (or 100) or it can extend only over a portion of the length and can correspond to certain sections such as the proximal section, one or more intermediate section 108, the distal region 1102, or a combination thereof. The polymeric outer region can comprise an elastomer such as, but not limited to, Hytrel, PET, polyimide, Pebax, polyurethane, silicone rubber, or the like, and can be coated with an additional anti-friction coating such as, but not limited to, silicone oil, silicone grease or gel, hydrophilic hydrogel, fluoropolymer, polyimide, or the like.

The distal coil 1102 is affixed, at its proximal end, to the distal end of the intermediate coil 108. The inner tube 104 is affixed to the distal coil 1102 such that most or nearly all the distal coil is controlled in expansion and contraction by the inner tube 104. The distal coil 1102 comprises the spaces 1110 which can range in magnitude from 0.0005 inches to about 0.020 inches or greater. In the illustrated embodiment, the coil spaces 1110 are about equal in width to the coil element diameter. The coil element diameters can range from about 0.0005 inches to about 0.010 inches and preferentially ranges from about 0.001 inches to about 0.007 inches in diameter. The coil materials can comprise materials such as, but not limited to, nitinol, polyimide, stainless steel, titanium, cobalt nickel alloy, or the like. The coil materials beneficially comprise material properties of low malleability and high spring hardness. The distal coil 1102 can be fabricated from flat or round wire.

Referring to FIGS. 11 and 2, the backbone 1104 is located on the side 234 of the steerable microcatheter 1100 where the inner tube 104 is disconnected from more proximal structures. Thus, axially oriented forces transmitted through the connected side 232 cause the spring coil 1102 to compress or expand longitudinally with more freedom and less restriction on the connected side 232, as imposed by the backbone 1104, than on the disconnected side 234. This results in an asymmetric force loading on the distal end and causes the distal end to deflect away from the longitudinal axis under control from the proximal end of the steerable microcatheter 1100.

Figure 12:
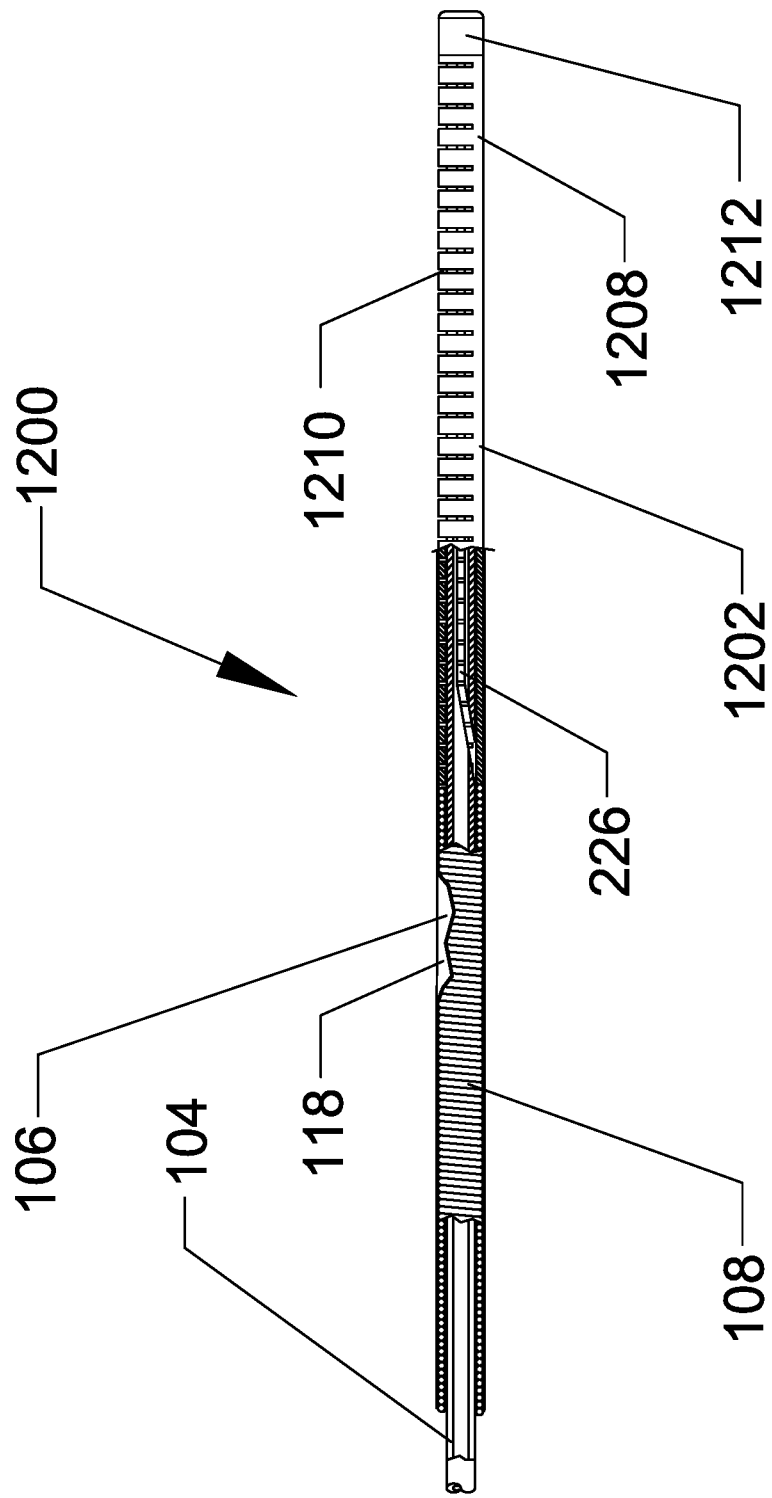
FIG. 12 illustrates a side, partial cutaway view of the distal end of a steerable microcatheter wherein the outer tube comprises a cut tube having a backbone and ribs.

FIG. 12 illustrates the distal end of a steerable microcatheter 1200 comprising the inner tube 104 further comprising the longitudinal slot 226, the proximal-to-distal-intermediate outer tube 108, the polymeric fluid barrier covering 118, the slip layer 106, a distal outer tube 1202 further comprising a plurality of lateral gaps 1210, a radiopaque marker 1212, and a backbone 1208.

Referring to FIG. 12, the distal outer tube 1202 can be fabricated as a tube comprising the slots 1210 or gaps that are imparted by way of EDM, wire EDM, laser cutting, photochemical etching, conventional machining, or the like. The proximal end of the distal outer tube 1202 is affixed to the distal end of the intermediate outer tube 108. The distal end of the distal outer tube 1202 is affixed to distal end of the inner tube 104 substantially distal to the distal end of the longitudinal slot 226 to prevent rotational and lateral relative movement at that point. The backbone 1208 forces asymmetric lengthening and compression of the gaps 1210 thus generating a lateral bend or curve out of the longitudinal axis in the distal outer tube 1202 when the inner tube is tensioned relative to the outer tube. The radiopaque marker 1212 is a cylindrical thin walled band, illustrated swaged into a circumferential groove at the distal end of the system.

FIG. 13A illustrates a side view of the inner tube 1300 of a steerable microcatheter. The inner tube 1300 comprises a proximal tube 1302, a distal bendable region 1304, further comprising a longitudinal slot 1306, a distal end tube 1308, a central lumen 1310, a plurality of flex enhancing cutouts 1316. Inner tube 1300 may also comprise an optional intermediate hyperflexible region 1320 which is detailed in FIG. 13B.

The flex enhancing cutouts 1316 can be disposed to open into the longitudinal slot 1306 or they can be disposed to open (not shown) to the exterior of the tube and not communicate with the longitudinal slot 1306, or be a combination thereof. The hyperflexible region 1320 can extend from about adjacent to the proximal end of the longitudinal slot 1306 to a region about 5, 10, 15, 20, or even 50-cm from the distal end of the inner tube 1300.

FIG. 13B illustrates a magnified view of the hyperflexible region 1320 further comprising slots 1322 and 1324 oriented in at least two different directions.

Referring to FIG. 13B, the slots 1324 and 1322 are radially offset from each other, and, as illustrated, are oriented orthogonally to each other. Each slot 1324 and 1322 may comprise one of a pair of slots coming in from the lateral direction to end in a central connector region (bridge 1314) that is not substantially favorable in bending to any particular direction and is still able to transmit compressive force, tensile force, and torque about the primary longitudinal axis. Thus the inner tube 1300 can bend around relatively sharp radii and still allow for inner tube movement relative to the outer tube to generate steering functionality. In the illustrated embodiment, the slots 1322 and 1324 arranged in repeat patterns of first 1322 and then 1324, after which the pattern repeats. This pattern could be modified to allow two or more of the same orientation slots to be grouped together. Furthermore, patterns could be applied that are oriented at other angles, for example 45 degrees, to the slots 1324 and 1322, thus providing additional or different flexibility.

FIG. 13C illustrates a lateral cross sectional view of inner tube 1300 at slot 1322, showing the lumen 1310, the bridge material 1314, and the slot 1323. The bridge material 1314 is preferably integral to the tubing 1402 and is formed by material being removed by laser cutting, EDM, or the like. The cross-sectional area of the bridge material needs to be sufficient to prevent failure, or preferably even yield when the outer tube 1400 is placed in tension or compression. For example, with stainless steel, which can have a tensile strength of, for example, 200,000-PSI, the cross sectional area will need to be sufficient to prevent yield or failure with a tension of, for example, 1 pound of force. Of course safety factors, usually 1.5 or higher, are always important, especially since the bridge material 1314 will also undergo torsion when the tube is bent or flexed.

Figure 14:
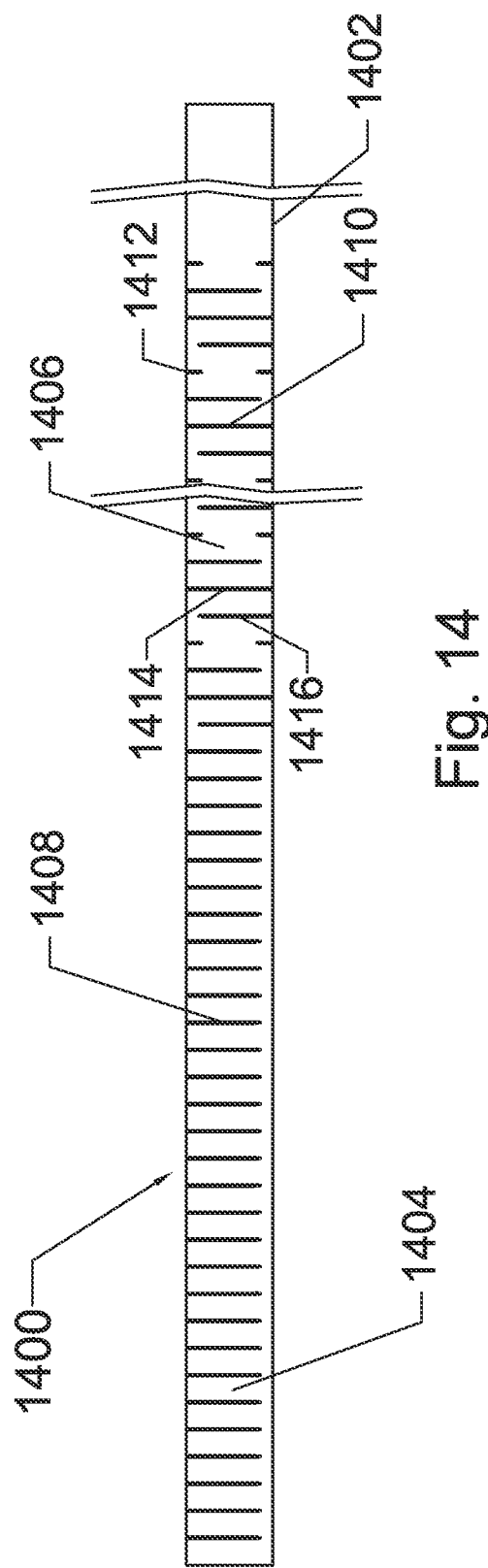
FIG. 14 illustrates a side view of an outer tube comprising a distal section of lateral slots configured to force bending in only one lateral plane and more proximally oriented slots configured to permit bending in multiple lateral planes.

FIG. 14 illustrates a side view of an outer tube 1400 further comprising a base tube 1402 having a lumen 1420 (not shown), a distal steering flex region 1404 further comprising a series of uniformly oriented slots 1408, and at least a first intermediate region 1406 further comprising a series of cutaways or slots 1410, 1412, 1414, and 1416.

Referring to FIG. 14, the slots 1410, 1412, 1414, and 1416 are arranged in a repeating sequence of 4 differently oriented slots extending the length of outer tube sufficient to allow for hyperflexibility. The hyperflexible region can comprise these slot patterns or the slot sequence and patterns which are the same as those shown in FIG. 13B (every other slot pair oriented radially 90° about the tube relative to an adjacent slot pair). The hyperflexible region can begin just proximal to the proximal end of the steering region 1404 and extend from 5 to 50 cm, or more, proximal to the proximal end of the bending region 1404. The number, spacing, and width of the lateral cuts can be pre-determined to allow for bending to a radius of curvature sufficient to track through specific vessels. Examples of some of the most tortuous vessels include the carotid siphon in the neck, which can have radii of curvature as small as 0.5-cm or less.

Further referring to FIG. 14, the distal steering region 1404 comprises a series of partial lateral cuts that can be terminated with a "T" or they can have no longitudinal component. The longitudinal component, which forms a "T" or an "H", depending on your point of view, helps to distribute stresses and minimizes the risk of yield when the device is curved. The device curves by allowing the slots 1408, in the steering region, to close or open, thus the steering occurs in one plane lateral to the longitudinal axis of the microcatheter. The width and number of partial lateral cuts in the steering region 1404 can be pre-determined to allow for bending through a certain minimum radius.

Thus, as described in relation to FIGS. 13A and 14, the steerable catheter comprises an outer tube having an outer tube wall, proximal end, a distal end and a lumen extending through the outer tube. The outer tube may be characterized by a distal segment, a proximal segment and a middle segment located between the distal segment and the proximal segment; and an inner tube having an outer tube wall, proximal end, a distal end and a lumen extending through the inner tube. The inner tube may also be characterized by a distal segment, a proximal segment and a middle segment located between the distal segment and the proximal segment. The inner tube is disposed within the outer tube such that the inner tube distal segment is disposed within the outer tube distal segment, the inner tube middle segment is disposed within the outer tube middle segment, and said inner tube proximal segment is disposed within the outer tube proximal segment. The inner tube is longitudinally fixed to the outer tube near the distal end of the outer tube, near the distal end of the outer tube distal segment. A hub is affixed to the proximal end of the inner tube and outer tube, and is operable to tension or compress the inner tube relative to the outer tube (or vice versa) to cause bending of the outer tube distal segment. To provide steering functionality, the outer tube has a first plurality of laterally oriented slots extending partway through the outer tube distal segment, wherein said first plurality of laterally oriented slits are aligned on one circumferential side of the outer tube thereby defining a spine running along a side of the tube opposite the slots and the inner tube wall has a longitudinal slot that divides the inner tube distal segment along a longitudinal axis. To provide extra flexibility to the structure in the middle segment, while maintaining column strength and tensile strength, the outer tube middle segment has a second plurality of laterally aligned slots extending partway through the outer tube, said second plurality of laterally aligned slots being non-aligned circumferentially, and the inner tube middle segment has a third plurality of laterally aligned slots extending partway through the inner tube, said second plurality of laterally aligned slots being non-aligned circumferentially. The longitudinal slot of the inner tube divides the tube into two axially oriented parts which are connected at the distal end of the inner tube, and one of said axially oriented parts includes a plurality of flex enhancing cutouts dispersed axially along said axially oriented part. The cutouts may be dispersed axially along an inner portion of said axially oriented part. The second plurality of slots are arranged in longitudinally aligned pairs, in a repeating pattern of a four differently oriented slots, or longitudinally aligned and radially dispersed pairs of slots, dispersed along the outer tube middle segment. The third plurality of slots (on the inner tube) are arranged in pairs, in a repeating pattern with a first pair of slots radially offset from a second pair of slots.

The hub can include an internal lumen capable of receiving a jack-screw traveler element or other actuator and preventing said jack-screw traveler element or actuator from rotating about the longitudinal axis of the hub, wherein the inner tube is constrained not move relative to the hub; a knob or other control mechanism configured for engagement with the jackscrew traveler element or actuator; and wherein the jack-screw traveler element or actuator affixed to the proximal end of the one of the outer tube or the inner tube, wherein the jack-screw traveler element or actuator comprises a traveler thread on at least a portion of a surface, and further wherein the inner tube can tensioned or compressed relative to the outer tube in response to movement of the jack-screw traveler, or wherein the outer tube can tensioned or compressed relative to the inner tube in response to movement of the jack-screw traveler.

Preferably, the slots in the middle segment of each tube are arranged to enhance flexibility in the middle segment of the microcatheter while avoiding a preferential off-axis bending, so that the middle segment will bend in any direction without preference to a particular bending direction or resistance to a particular bending direction. This may be accomplished by locating the pairs of slots 1322, 1323 (and resultant bridges 1314) in the inner tube middle segment relative to slots 1412 (or pairs of slots) in the outer tube middle segment such that slot pairs in the inner tube are radially displaced from slots, or slot pairs, in the outer tube. In other words, the plurality of laterally oriented slots in the outer tube middle segment defines a bridge portion of the outer tube middle segment and is longitudinally aligned with one of the pairs of laterally oriented slots in the inner tube middle segment which define bridges in the inner tube middle segment, and disposed outer tube middle segment such that the bridge portion is circumferentially displaced from the bridge portions of the inner tube middle segment.

In some embodiments, instead of having the inner tube or rod cut into a control rod and a keeper or stay, the stay or keeper can be eliminated and the inner tube or rod separated into two or more control rods that can be affixed to the apparatus at a point distal to the bendable region. The proximal ends of the control rods extend all the way into the hub and are affixed to separate actuators, which can be jackscrews, hydraulic actuators, pneumatic actuators, magnetic actuators, or the like. Since the distal end of the device can have various bending characteristics and symmetry, it is beneficial that each control rod have a separate actuator that can move at different axial distances given a single control input by the user. For example, two jackscrews can comprise different thread pitches to accommodate off-center motion at the distal bendable region. Thus a push-pull force balance is applied to the distal end to enhance the amount of flexural modulus and increase the bending forces that can be generated by the system. Control rods that are not used or actuated at the proximal end can serve as keepers or stays to maintain the radial position of the control rods in an off-center configuration.

The embodiments presented herein describe a system that does not use pull wires. No side lumens are required in either the outer tube or the inner tube. Such side lumens, as found in certain prior art catheters, require extensive cross-sectional area be used to surround the side lumens and take away from the potential area for the central lumen since the outside extent of the catheter is limited. The use of pull wires requires such as those in certain prior art catheters, retaining these structures along one side of the outer tube may be difficult or impossible. Side lumens or channels are necessary to retain a pull wire or control rod in the correct location so as to provide correct off center forces to bend the distal end. The side lumens are also necessary to keep the control rod or pull wires out of the central lumen which needs to remain open and substantially circular. The system disclosed herein, however, retains a high degree of column strength, maximum torquability, the largest possible central lumen, and a very strong control and steering function or capability. Furthermore, the side lumens or channels are necessary to maintain spatial (rotational orientation) for the articulating distal end of the device. Without the side lumens or channels permitting axial slidability but generating radial retention, the pull wires or pushrods would be free to migrate around within the central lumen of the device and could bend the device in an unwanted direction. Long microcatheters with relatively small cross-sectional areas are highly subject to torque and rotational misalignment and some method must be employed to retain the correct circumferential location of the articulating apparatus. It is possible, however to divide the central lumen into one or more channels thus forming a dual lumen microcatheter, a tri-lumen microcatheter, a quad lumen microcatheter, or the like.

Furthermore, a pull-wire as used in prior art devices is incapable of generating compression against the distal end of the device so a pull-wire could not, under compression, move or articulate the distal end of the device. The pull-wire, under tension, can move or articulate the distal end and would require some sort of counterforce such as an opposing pull-wire, shape memory metal, or spring return biasing to move the distal end in the reverse direction.

However, a tubular or cylindrical (substantially no lumen) central control device can maintain its structure in compression, maintain circumferential location within the outer cylindrical, axially elongate tube, maintain precise control, maintain sufficient tensile strength to exert forces, and maintain a central lumen larger than any other type of steerable device. The resistance to buckling occurs even when the inner tube is slotted longitudinally because the inner tube is constrained within the outer tube using very tight tolerances that will not let the inner tube bend out of its straight orientation, even under compression.

The present inventions may be embodied in other specific forms without departing from its spirit or essential characteristics. These devices lend themselves to motorized control and robotic control. The motorized or robotic control can be wholly exercised by a human operator, partially by the human operator and artificial intelligence (AI), or wholly by AI. The motorized system can be powered using linear actuators, stepper motor systems, pneumatics, hydraulics, magnetic couplings, and the like. Feedback can comprise fluoroscopic imaging systems, ultrasound imaging systems, magnetic resonance imaging systems, PET scans, X-ray based imaging such as fluoroscopy, and the like. Angiograms can be taken to help create roadmaps for catheter advancement. A catheter system such as this can generally be controlled using a longitudinal axis actuator, a rotary axis actuator, and a deflection actuator. Fine adjust systems can piggyback off of coarse system placement actuators and guides. The longitudinal axis travel can range from about 5-cm up to about 300-cm or more.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:
1. A steerable catheter comprising:
an outer tube having an outer tube wall, an outer tube proximal end, an outer tube distal end and an outer tube lumen extending therethrough, said outer tube characterized by an outer tube distal segment, an outer tube proximal segment, and an outer tube middle segment located between said outer tube distal segment and said outer tube proximal segment; and
an inner tube having an inner tube wall, an inner tube proximal end, an inner tube distal end and an inner tube lumen extending therethrough, said inner tube characterized by an inner tube distal segment, an inner tube proximal segment, and an inner tube middle segment located between said inner tube distal segment and said inner tube proximal segment;
said inner tube disposed within the outer tube such that the inner tube distal segment is disposed within the outer tube distal segment, the inner tube middle segment is disposed within the outer tube middle segment, and said inner tube proximal segment is disposed within the outer tube proximal segment;
said inner tube being longitudinally fixed to the outer tube proximate the distal end of the outer tube proximate a distal end of the outer tube distal segment; and
a hub affixed to the proximal end of the inner tube and outer tube, said hub operable to tension or compress the inner tube relative to the outer tube to cause bending of the outer tube distal segment; wherein
the outer tube has a first plurality of laterally oriented slots extending partway through the outer tube distal segment, wherein said first plurality of laterally oriented slits are aligned on one circumferential side of the outer tube thereby defining a spine running along a side of the tube opposite the slots;
the inner tube wall has a longitudinal slot that divides the inner tube distal segment along a longitudinal axis, into two axially oriented parts which are connected at the distal end of the inner tube, and one of said axially oriented parts includes a plurality of flex enhancing cutouts dispersed axially along an inner portion of said axially oriented part;
the outer tube middle segment has a second plurality of laterally oriented slots extending partway through the outer tube, said second plurality of laterally oriented slots being non-aligned circumferentially; and
the inner tube middle segment has a third plurality of laterally oriented slots extending partway through the inner tube, said second plurality of laterally oriented slots being non-aligned circumferentially.

2. The steerable catheter of claim 1 wherein the second plurality of laterally oriented slots are arranged in a repeating pattern of four differently oriented slots dispersed along the outer tube middle segment.

3. The steerable catheter of claim 1 wherein the second plurality of laterally oriented slots are arranged in longitudinally aligned pairs, in a repeating pattern of four differently oriented pairs of slots dispersed along the outer tube middle segment.

4. A steerable catheter comprising:
an outer tube having an outer tube wall, an outer tube proximal end, an outer tube distal end and an outer tube lumen extending therethrough, said outer tube characterized by an outer tube distal segment, an outer tube proximal segment, and an outer tube middle segment located between said outer tube distal segment and said outer tube proximal segment; and
an inner tube having an inner tube wall, an inner tube proximal end, an inner tube distal end and an inner tube lumen extending therethrough, said inner tube characterized by an inner tube distal segment, an inner tube proximal segment, and an inner tube middle segment located between said inner tube distal segment and said inner tube proximal segment;

said inner tube disposed within the outer tube such that the inner tube distal segment is disposed within the outer tube distal segment, the inner tube middle segment is disposed within the outer tube middle segment, and said inner tube proximal segment is disposed within the outer tube proximal segment;

said inner tube being longitudinally fixed to the outer tube proximate the distal end of the outer tube proximate a distal end of the outer tube distal segment; and a hub affixed to the proximal end of the inner tube and outer tube, said hub operable to tension or compress the inner tube relative to the outer tube to cause bending of the outer tube distal segment; wherein the outer tube has a first plurality of laterally oriented slots extending partway through the outer tube distal segment, wherein said first plurality of laterally oriented slits are aligned on one circumferential side of the outer tube thereby defining a spine running along a side of the tube opposite the slots;

the inner tube wall has a longitudinal slot that divides the inner tube distal segment along a longitudinal axis;

the outer tube middle segment has a second plurality of laterally oriented slots extending partway through the outer tube, said second plurality of laterally oriented slots being non-aligned circumferentially; and the inner tube middle segment has a third plurality of laterally oriented slots extending partway through the inner tube, said second plurality of laterally oriented slots being non-aligned circumferentially; wherein the second plurality of laterally oriented slots are arranged in a repeating pattern of four differently oriented slots dispersed along the outer tube middle segment and the third plurality of laterally oriented slots (on the inner tube) are arranged in pairs, in a repeating pattern with a first pair of slots radially offset from a second pair of slots.

5. The steerable catheter of claim 4, wherein, each of the plurality of laterally oriented slots in the outer tube middle segment a bridge portion of the outer tube middle segment and is longitudinally aligned with one of the pairs of laterally oriented slots in the inner tube middle segment which define bridge portions in the inner tube middle segment, and disposed outer tube middle segment such that the bridge portion of the outer tube middle segment is circumferentially displaced from the bridge portions of the inner tube middle segment.

6. The catheter of claim 1, wherein the hub comprises:
a hub body having an internal lumen;
a jack-screw traveler element or other actuator disposed within the internal lumen;
the hub body and internal lumen configured for receiving the jack-screw traveler element or other actuator and preventing the jack-screw traveler element or actuator from rotating about the longitudinal axis of the hub, wherein the inner tube is constrained to not move relative to the hub; and
a knob or other control mechanism configured for engagement with the jackscrew traveler element or other actuator; and wherein the jack-screw traveler element or other actuator is affixed to the proximal end of the one of the outer tube or the inner tube, wherein the jack-screw traveler element or other actuator comprises a traveler thread on at least a portion of a surface, and further wherein the inner tube can be tensioned or compressed relative to the outer tube in response to movement of the jack-screw traveler or other actuator, or wherein the outer tube can tensioned or compressed relative to the inner tube in response to movement of the jack-screw traveler or other actuator.

7. The catheter of claim 4, wherein the hub comprises:
a hub body having an internal lumen;
a jack-screw traveler element or other actuator disposed within the internal lumen;
the hub body and internal lumen configured for receiving the jack-screw traveler element or other actuator and preventing the jack-screw traveler element or actuator from rotating about the longitudinal axis of the hub, wherein the inner tube is constrained to not move relative to the hub; and
a knob or other control mechanism configured for engagement with the jackscrew traveler element or other actuator; and wherein the jack-screw traveler element or other actuator is affixed to the proximal end of the one of the outer tube or the inner tube, wherein the jack-screw traveler element or other actuator comprises a traveler thread on at least a portion of a surface, and further wherein the inner tube can be tensioned or compressed relative to the outer tube in response to movement of the jack-screw traveler or other actuator, or wherein the outer tube can tensioned or compressed relative to the inner tube in response to movement of the jack-screw traveler or other actuator.

* * * * *